United States Patent
Boas

(10) Patent No.: US 6,516,214 B1
(45) Date of Patent: Feb. 4, 2003

(54) DETECTION OF STROKE EVENTS USING DIFFUSE OPTICAL TOMOGRAPHY

(75) Inventor: David Alan Boas, Newmarket, NH (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/491,595

(22) Filed: Jan. 25, 2000

Related U.S. Application Data
(60) Provisional application No. 60/178,526, filed on Jan. 24, 2000.

(51) Int. Cl.[7] ............................................. A61B 6/00
(52) U.S. Cl. ..................... 600/431; 600/473; 600/477; 600/310
(58) Field of Search ................................ 600/477, 473, 600/476, 431, 310

(56) References Cited

U.S. PATENT DOCUMENTS

| | | | |
|---|---|---|---|
| 5,377,681 A | * 1/1995 | Drane | 128/653.4 |
| 5,458,128 A | * 10/1995 | Polanyi et al. | 128/654 |
| 5,706,821 A | * 1/1998 | Matcher et al. | 128/665 |
| 5,803,909 A | 9/1998 | Maki et al. | |
| 5,954,053 A | 9/1999 | Chance et al. | |
| 5,987,346 A | * 11/1999 | Benaron et al. | 600/407 |
| 5,999,841 A | * 12/1999 | Aoyagi et al. | 600/431 |
| 6,161,031 A | * 12/2000 | Hochman et al. | 600/407 |
| 6,223,069 B1 | * 4/2001 | Pfeiffer et al. | 600/431 |

FOREIGN PATENT DOCUMENTS
WO    WO 98/08434    3/1998

OTHER PUBLICATIONS

"Impedance Method for Localizing Brain Structures"; B. Robinson and H. Tompkins; Archives of Neurology, vol. 10; 1964.

"Locating Brain Structures, Extensions in Impedance Method"; Bryan W. Robinson, James S. Bryan and H. Enger Rosvold; Arch Neurol—vol 13; Nov. 1965.

"The Value of Impedance Measurements to Aid in the Localisation in Stereotactic Surgery"; G. Dierseen and E. Marg; 2nd Symp. Stereoencephalotomy, Copenhagen, 1965.

"Impedance and Phase Angle as a Locating Method in Human Stereotaxic Surgery"; Lauri Laitinen, Gunnar Johansson and Pentti Sipponen; Neurological Clinic, University Central Hospital, Helsinki, Finland.

"Tissue Impedance Along Probe Trajectories in Thalamotomy"; J. Aguilar, S. Tachibana and L. Birzis; 4th Symp. Int. Soc. Res. Stereoencephalotomy, New York, 1970.

Edwards et al., "Cotside Measurement of Cerebral Blood . . . ," The Lancet, pp. 770–771, 1988.

* cited by examiner

Primary Examiner—Marvin M. Lateef
Assistant Examiner—Devaang Shah
(74) Attorney, Agent, or Firm—Fish & Richardson P.C.

(57) ABSTRACT

The invention relates to a method of using diffuse optical tomography and a blood-borne dye in a stroke patient, or a patient suspected of having a stroke, to detect ischemic events or bleeds in the brain.

49 Claims, 12 Drawing Sheets

$$g(i,j) = \underbrace{P_L \, C_{LF} \, T_{LF} \, C_{FT}}_{S^i} \, f(i,j) \, \underbrace{C_{TF} \, T_{DF} \, C_{FD} \, \gamma_{PE} \, A}_{D^j}$$

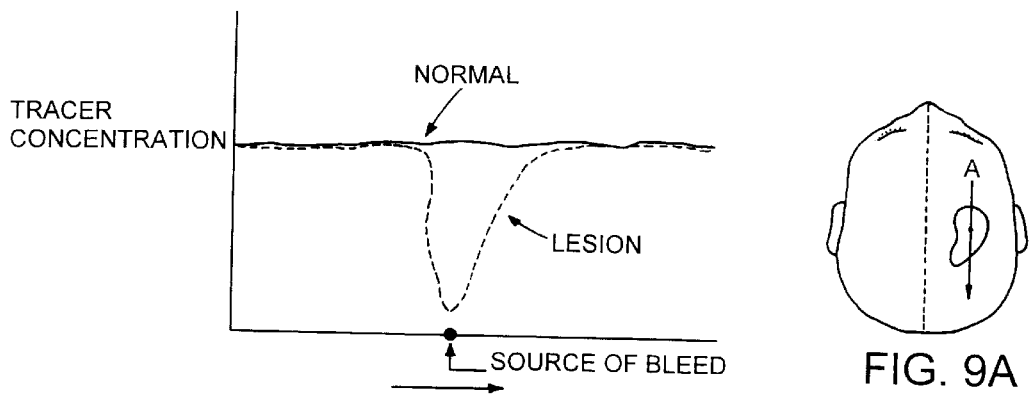
FIG. 9B
FIG. 9A
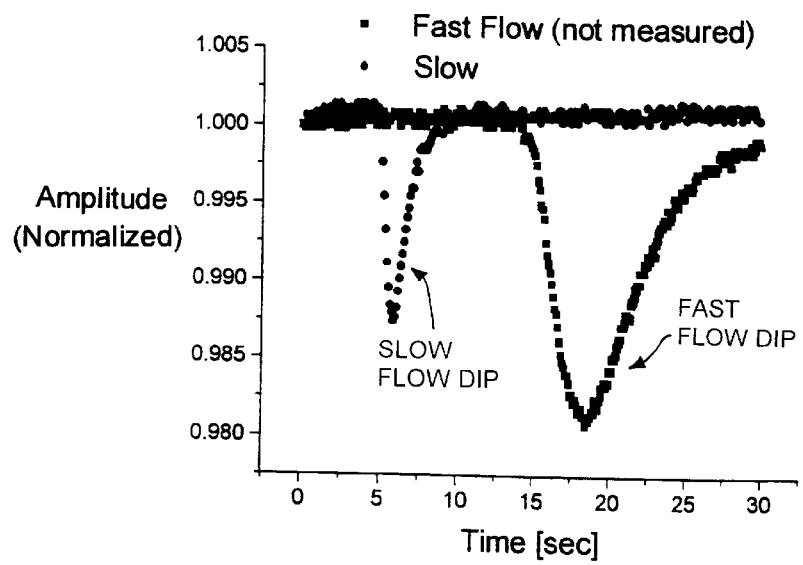
FIG. 10

Wavelength = 780 nm

Before calibration

After calibration

Wavelength = 830 nm

Before calibration

After calibration

DETECTION OF STROKE EVENTS USING DIFFUSE OPTICAL TOMOGRAPHY

CROSS-REFERENCE TO RELATED APPLICATIONS

This application claims priority from U.S. Provisional Application No. 60/178,526 filed Jan. 24, 2000, entitled "Detection of Stroke Events Using Diffuse Optical Tomography," with David Alan Boas as inventor.

STATEMENT AS TO FEDERALLY-SPONSORED RESEARCH

This invention was made with Government grants from the National Institutes of Health under grant 1R29NS38842 A01 and the U.S. Army under contract DAMD17-99-2-9001. The Government has certain rights in the invention.

FIELD OF THE INVENTION

The invention is in the field of diffuse optical tomography and stroke.

BACKGROUND OF THE INVENTION

Victims of stroke caused by an ischemic event in the brain can benefit from treatment with recombinant tissue plasminogen activator, a thrombolytic drug, within three hours of the ischemic event. On the other hand, if the stroke is caused by a bleed instead of an ischemic event, thrombolytic drugs are contraindicated. Thus, a quick and efficient means of distinguishing an ischemic event from a bleed in a stroke victim would aid a health care provider in managing the treatment of stroke victims. Furthermore, treatment protocols need to be tailored to individual patients. Therefore, continuous monitoring of cerebral perfusion would enable the health care provider to more effectively guide treatment in a patient with a specific pathology.

Diffuse optical tomography (DOT) refers to various non-invasive methods of imaging different tissues of a body or organ. Generally, DOT relies on the emission of light from a light source into the body, then detecting the light scattered from various tissues of the body. For example, since light scattered by hemoglobin in blood differs from light scattered by other tissues, DOT has been applied to the imaging of blood within the body. In addition, because the absorption of light by deoxyhemoglobin is different from the absorption of light by oxyhemoglobin, DOT has been used to locate areas of high or low oxygenation in the body by determining decreases or increases in the intensity of scattered light. However, the application of DOT in various imaging scenarios in the clinic has been limited by the inability to detect light scattered by deep tissues. This can be due to either the inability of the emitted light to reach deep tissues, or the inability to detect and measure the weak intensity of light scattered by the deep tissues (i.e., no measurable contrast between scattered light and background).

SUMMARY OF THE INVENTION

The invention is based on the recognition that ischemic events deep in the brain can be detected using DOT to monitor collateral blood flow abnormalities in cortical regions of the brain arising from the deep ischemic events using blood-borne tracer dyes (also called contrast agents or tracers). By extrapolating information from the cortical regions, deep ischemic events as well as cortical ischemic events in the brain can be monitored even if the light used for DOT does not penetrate into the deep portions of the brain, or if the contrast in the light scattered from blood and solid tissues in the deep portions of the brain is not easily detected.

The invention is also based on the recognition that a brain bleed can be imaged by DOT using a blood-borne tracer dye and detecting a localized region of a lower concentration of dye or of no dye at all, as compared to an adjacent region in the brain. The imaging of a brain bleed is made possible by recognizing that blood vessel constriction and clotting at the site of the bleed will inhibit the dye from infiltrating the region of the bleed while adjacent regions are unaffected. In addition, the use of a tracer dye increases the contrast in light scattered by blood versus solid tissue deep in the brain, thereby allowing blood volume to be imaged even where the intensity of scattered light is weak.

Accordingly, the invention features a method of detecting an ischemic event in a brain in a subject, using a first criterion, by (1) administering a dye bolus into the bloodstream of the subject; (2) directing light into the brain of the subject; (3) detecting light emitted from the brain over time at a detection location, the dye being present in the brain for at least a portion of the detection time, and the light emitted from the brain in the presence of the dye being different from the light emitted from the brain in the absence of the dye, the magnitude of the difference corresponding to the concentration of the dye; (3) establishing a reference time period corresponding to the time a peak concentration of a dye bolus takes to reach the detection location in a normal brain; (4) determining a subject time period corresponding to the time a peak concentration of the dye bolus takes to reach the detection location in the subject; and (5) comparing the subject time period with the reference time period, where a subject time period 1 or more seconds longer than the reference time period indicates an ischemic event in the brain. If the subject time period is 2 or more seconds longer than the reference time period, then an ischemic event in a deep portion of the brain is indicated.

In another aspect, the invention includes a method of detecting an ischemic event in a brain in a subject, using a second criterion, by (1) administering a dye bolus into the bloodstream of the subject; (2) directing light into the brain of the subject; (3) detecting light emitted from the brain over time at a detection location, the dye being present in the brain for at least a portion of the detection time, and the light emitted from the brain in the presence of dye being different from the light emitted from the brain in the absence of the dye, the magnitude of the difference corresponding to the concentration of the dye; (4) establishing a peak reference concentration of a dye bolus administered to a subject with a normal brain at the detection location; (5) determining a peak subject concentration of the dye bolus at the detection location; and (6) comparing the peak subject concentration with the peak reference concentration, where a peak subject concentration below the peak reference concentration indicates an ischemic event in the brain. If the peak subject concentration is below the peak reference concentration but at least 50% of the peak reference concentration, then an ischemic event in a deep portion of the brain is indicated.

The invention also includes a method of detecting an ischemic event in a brain in a subject, using a third criterion, by (1) administering a dye bolus into the bloodstream of the subject; (2) directing light into the brain of the subject; (3) detecting light emitted from the brain over time at a detection location, the dye being present in the brain for at least a portion of the detection time, and the light emitted from the brain in the presence of dye being different from the light emitted from the brain in the absence of the dye, the magnitude of the difference corresponding to the concentration of the dye; (4) establishing a reference time period corresponding to the time for the concentration of a dye bolus to vary from a threshold (e.g., 10, 5, 2, or 1% by volume) concentration to a peak concentration and back to the threshold concentration at the detection location in a normal brain; (5) determining a subject time period corresponding to the time for the concentration of the dye to vary from the threshold concentration to a peak concentration and back to the threshold concentration at the detection location; and (6) comparing the subject time period with the reference time period, where a subject time period longer than the reference time period indicates an ischemic event in the brain. If the subject time period is at least 2 seconds longer than the reference time period, then an ischemic event in a deep portion of the brain is indicated.

In still another aspect, the invention includes a method of detecting an ischemic event in a brain in a subject, using a fourth criterion, by (1) administering a dye bolus into the bloodstream of a subject; (2) directing light into the brain of the subject; (3) detecting light emitted from the brain over time at a detection location, the dye being present in the brain for at least a portion of the detection time, and the light emitted from the brain in the presence of the dye being different from the light emitted from the brain in the absence of the dye, the magnitude of the difference corresponding to the concentration of the dye; (4) establishing a reference map of cortical blood flow in a normal brain; (5) obtaining a subject map of cortical blood flow in the subject; and (6) comparing the reference map with the subject map, where a continuous region of decreased blood flow in the subject map, compared to the reference map indicates an ischemic event in the brain. If the continuous region of decreased blood flow is at least 20 mm at the longest diameter, then an ischemic event in a deep portion of the brain is indicated. In addition, this method can further include (7) comparing the position of the region of decreased blood flow with a map of known brain vasculature; and (8) extrapolating the position of the ischemic event in the brain of the subject.

In addition, the invention includes a method of detecting an ischemic event in a brain in a subject using any combination (e.g., all) of the criteria specified above. The methods described above also need not specify all the steps; only the last comparing step is required.

The invention further includes a method of detecting a brain bleed in a subject by (1) administering a dye into the bloodstream of the subject; (2) directing light from a light source into the brain of the subject; (3) detecting light emitted from the brain while the dye is present in a portion of the brain, the light emitted from the brain in the presence of the dye being different from the light emitted from the brain in the absence of the dye, the magnitude of the difference corresponding to the concentration of the dye, and the detecting step being performed while the dye is detectable in the blood circulation of the subject; and (4) determining the concentration of the dye in the portion of the brain, where a region of the portion with a lower concentration of the dye than an adjacent region of the portion indicates a brain bleed.

In another aspect, the invention includes a method of detecting a brain bleed in a subject by administering a dye into the bloodstream of the subject; (2) directing light from a light source into the brain of the subject; (3) detecting light emitted from the brain while the dye is present in a portion of the brain, the light emitted from the brain in the presence of the dye being different from the light emitted from the brain in the absence of the dye, the magnitude of the difference corresponding to the concentration of the dye, and the detecting step being performed after the initial dye concentration in the blood circulation of the subject has been reduced; and (4) determining the concentration of the dye in the portion of the brain, where a region of the portion with a higher concentration of the dye than an adjacent region of the portion indicates a brain bleed.

In the methods of the invention, the dye can be indocyanine green or any other suitable dye described herein, the difference in light can be the amplitude of light, and the subject can be a mammal (e.g., a human). In addition, the methods can include directing light into the brain through the scalp of the subject from a plurality of light sources and detecting light emitted from the brain using a plurality of photodetectors (e.g., charged-coupled devices).

In the methods, light can be emitted and detected using a system including (1) at least two optical sources which during operation emit light into a sample at spatially separated locations; (2) at least two optical detectors positioned to receive light emitted from the sample at spatially separated locations in response to the light emitted from the sources, wherein the signal g(i,j) produced by the $j^{th}$ detector in response to the optical radiation from the $i^{th}$ source can be expressed as $g(i,j)=S^iD^jf(i,j)$, where f(i,j) depends only on the properties of the head of the subject, $S^i$ is a coupling coefficient for the $i^{th}$ source, and $D^j$ is a coupling coefficient for the $j^{th}$ detector; and (3) an analyzer which during operation calculates the value of the product $S^iD^k$ for at least one of the source-detector pairs based on the signals produced by the detectors and simulated values of f(i,j) corresponding to a model of the optical properties of the sample.

Further, the light can be directed by at least two optical sources and detected by at least two optical detectors, the sources coupling light into the brain at spatially separated locations, and the detectors positioned to receive light emitted from the sample at spatially separated locations and generating signals in response to the light from the sources. In such a situation, the method can further include (1) providing the signals generated by the detectors, wherein the signal g(i,j) generated by the $j^{th}$ detector in response to the optical radiation from the $i^{th}$ source can be expressed as $g(i,j)=S^iD^jf(i,j)$, where f(i,j) depends only on the properties of the sample, $S^i$ is a coupling coefficient for the $i^{th}$ source, and $D^j$ is a coupling coefficient the $j^{th}$ detector; and (2) calculating the value of the product $S^iD^k$ for at least one of the source-detector pairs based on the signals generated by the detectors and simulated values of f(i,j) corresponding to a model of the optical properties of the brain.

A "normal" brain or region of a brain as used herein is a brain or region suitable to serve as a control or reference tissue for testing of potentially affected tissue in a subject brain. Thus, a normal or reference brain or region can be a different brain than that of the brain of a subject under DOT examination, or the same brain as that of the subject. Where the normal brain is the same as the subject's, the control or reference tissue can be a matched, symmetric region (e.g., right versus left hemisphere), or a region adjacent to the potentially affected tissue. Due to calibration considerations (discussed below), regions adjacent to the potentially affected tissue serve as better normal portions of the brain than symmetric regions, which in turn are better normal portions than regions of a different brain in a different individual.

A "deep" portion or region of a brain is greater than 1 cm below the inner surface of the skull.

The methods of the invention provide for a quick, non-invasive means of detecting and distinguishing a bleed or ischemic event in the brain of a stroke patient or suspected stroke patient. The methods are particularly applicable for a patient exhibiting a recent onset of one or more symptoms of stroke. In such a patient, distinguishing a bleed from an ischemic event in the shortest amount of time is important for determining the optimal treatment for the patient during the critical first few hours after an ischemic stroke. In addition, the methods can be applied continuously to monitor the development of a stroke in a patient for fine tuning of the treatment.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 9A is a schematic representation of a human head, showing a brain bleed (clear region) surrounding a source bleed source (dot), while a dye bolus (hatched region) is present in the brain. The clear region represents a decreased concentration of dye due to an inability of the dye to infiltrate the bleed.

FIG. 9B is a graph of position along line A versus tracer concentration for the abnormality seen in FIG. 9A.

FIG. 10 is a graph of time versus amplitude in a DOT experiment.

FIG. 16A is a perspective view of the cap. FIG. 16B is a top view of the cap. FIG. 16C is a portion of a cross-sectional view of the cap taken along line A—A in FIG. 16B, as positioned on the scalp.

DETAILED DESCRIPTION

Figure 1:
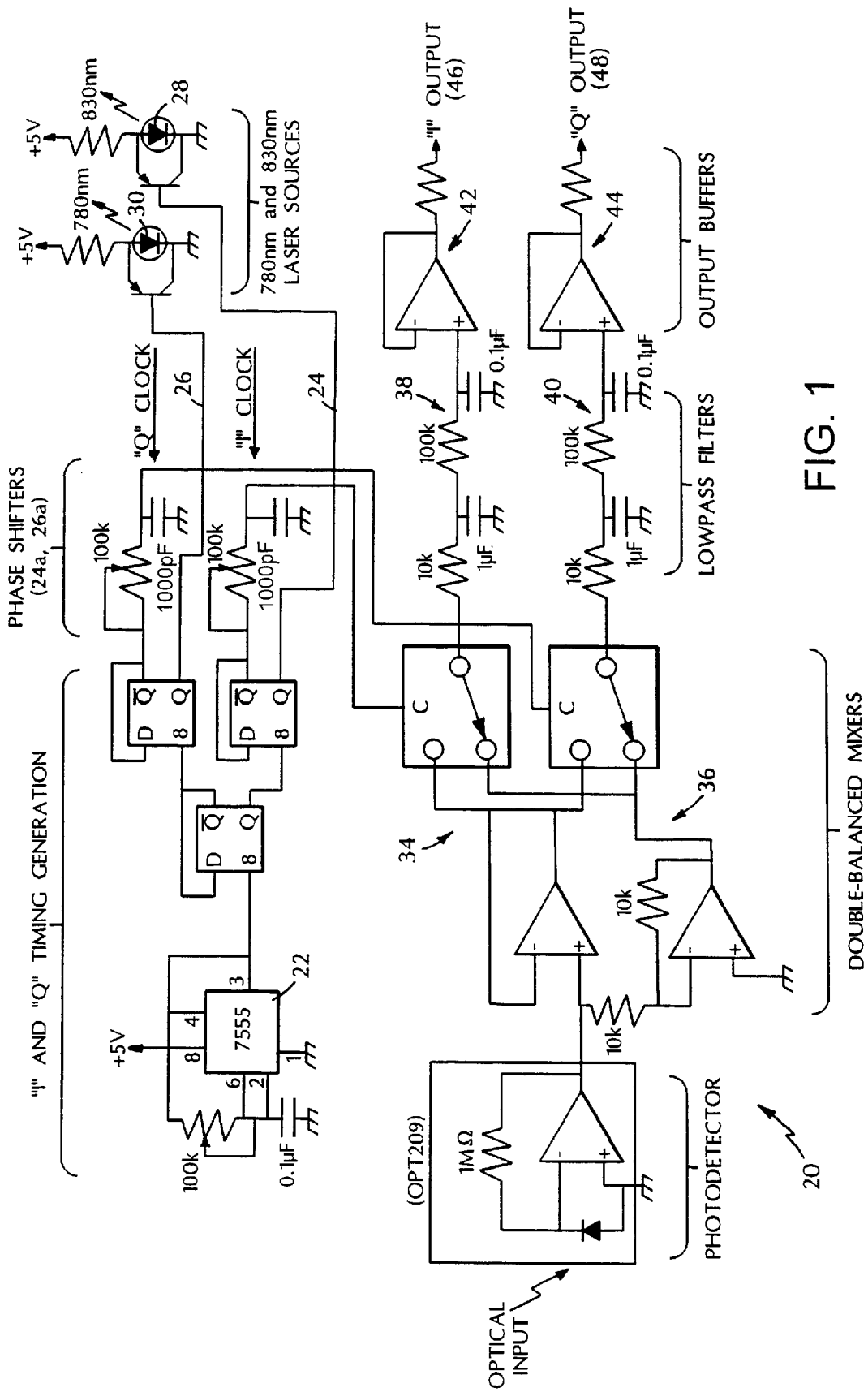
FIGS. 1–3 are schematic drawings of systems suitable for implementing the methods of the invention.

The invention relates to the use of diffuse optical tomography for detecting a bleed or ischemic event in a brain, or distinguishing one from the other. The various light emitters and detectors, dyes, and algorithms used for carrying out DOT are discussed below.

Introduction and General Considerations

The difficulty with using light to detect and monitor an ischemic stroke, relative to a brain bleed, arises from the significantly smaller abnormal blood volume associated with ischemia than the abnormal blood volume associated with a brain bleed. Normally, perfused brain tissue contains between 5–10% blood by volume. On the other hand, the region of a bleed contains about 100% blood. Further, as the bleed matures, the plasma diffuses away, leaving a pool of blood with a greater concentration of hemoglobin and thus higher optical absorption. Therefore, a bleed will offer an intrinsic contrast exceeding a factor of 10–20, and is detectable by static DOT imaging of blood.

For an ischemic stroke, the blood volume may change by as little as a factor of 2 because ischemia is characterized by reduced, not increased, perfusion. In addition, the oxygen saturation will likely drop because of a higher oxygen extraction fraction resulting from the reduced perfusion. Depending on the wavelength of the measurement, the contrast due to a decrease in the ratio of oxyhemoglobin to deoxyhemoglobin can vary from −50% at 750 nm to +50% at 850 nm. The significantly smaller contrast of an ischemic stroke relative to a bleed has led many to believe that ischemic stroke cannot be detected, monitored, or imaged using DOT.

The problem is overcome by recognizing that the reduced perfusion of a deep ischemic stroke has collateral effects extending to the cortex (see Example 1 below). Using hemodynamic magnetic resonance imaging (MRI), it was shown that the transit of blood in the cortical region adjacent to an ischemic stroke was delayed relative to brain tissue that is not at risk for infarct. The magnitude of the delay, as well as the spatial extent (size) of the blood flow abnormality can indicate the severity of an ischemic stroke. Changes in these parameters can also provide valuable feedback on the natural evolution of a stroke and the response of a stroke to treatment.

When light of a certain wavelength (e.g., near infrared light) is shone on a body surface, a small percentage of the light is reflected by the surface while most of the light enters the body. Most of the light entering the body then travels small distances before its direction is randomized by multiple scattering events caused by materials within the body (including tissues and contrast agents). As the light migrates through tissues, there is a small probability that a photon will be absorbed, as compared to a scattering event. Since the scattering probability is much greater than the absorption probability in the transmission window between 700 nm and 900 nm, a small but detectable amount of light is able to migrate through the scalp and skull into the brain and back out to the surface of the scalp. The volume sampled by the scattered light depends on the positioning of the light emitter(s) and collector(s) relative to each other. If the absorption probability increases, e.g., in the presence of an absorbing dye, within a tissue, then the amount of light detected will decrease.

In addition, a major problem in implementing optical methods for monitoring brain hemodynamics is distinguishing scalp signals from brain signals. This is true with static measurements of blood volume (total hemoglobin concentration) and oxygen saturation (proportion of total hemoglobin that is oxyhemoglobin), as well as dynamic bolus kinetic measurements of blood flow. Three approaches can be used to help solve this problem: (1) small versus large separation—compare optical measurements made with a 1 cm optode separation to that made with a separation greater than 2 cm; (2) left vs right difference—compare measurements made at symmetrical positions on the right and left hemispheres of the head; and 3) press the optodes firmly against the scalp.

(1) The measurement made with the small optode separation will only see the scalp and skull while the measurement made with the larger separation will see the scalp, skull, and brain (see Example 6 below). Typically, blood is seen to arrive in the cortex a few seconds before it arrives in the scalp. This is confirmed by seeing a signal change with the larger separation measurement a few seconds before seeing a change with the smaller separation measurement. Thus, any delay in the arrival and/or transit of blood to the cortex can be gauged by the comparison of the larger separation measurement to the small separation measurement.

(2) The hemodynamics on the left and right sides of the head are symmetric for healthy individuals. Any asymmetry is indicative of an abnormality.

(3) Pressing the optodes firmly against the head will blanch the scalp of blood and thus reduce the sensitivity to scalp signals.

Another problem arises from the blocking of optodes by hair. One solution for this problem is to provide a downward force on the optodes so that the optodes make contact with the skin surface. The optodes can then be moved from sided to side along the surface of the scalp to displace any hair blocking the optodes.

Another implementation strategy involves extracting small signal changes resulting from small concentrations of the vascular contrast agent or dye. While measurements of light intensity or amplitude at the optode emitter wavelength are suitable in DOT, measurements at a wavelength different from the optode emitter wavelength are also possible if the dye is a fluorophore. Detection at the fluorophore's emitter wavelength can be used to measure relatively small concentrations of the dye within the blood. Thus, the main advantage of fluorescence detection is that smaller concentrations can be injected into the subject for DOT measurements, thereby permitting repeated injections every minute rather than every 10 minutes, as is typical with an absorptive contrast agent. The delay in re-administration of an absorptive dye such as indocyanine green (ICG) is necessary to allow the dye to be metabolized by the liver. Without clearance of the dye by the liver, the baseline level of dye in the circulation would be too high for detecting the next bolus injected into the patient. Of course, nothing precludes simultaneous monitoring at both an optode emitter wavelength and a fluorophore emitter wavelength. Such simultaneous monitoring can be used when a single contrast agent having both significant absorption at the optode emitter wavelength and fluorescence wavelength is injected into a patient as a bolus. Alternatively, simultaneous monitoring can be useful if an absorptive dye and a fluorescent dye are injected into the patient, either at the same time or at different times.

The problem with direct DOT imaging of deep tissue within the adult human brain is that very few photons actually reach the deep tissue and then escape the head to be detected. Photon counting detection methods provide the best signal-to-noise ratio when the number of photons detected per second is small (typically less than $1 \times 10^6$ per second). However, when using light sources with an average power of 0.1 mW or smaller, the number of photons that reach the center of the brain and escape from the body is much less than the typical background noise of 10 photons per second. This problem is best solved by using lasers with powers greater than 1 W, but fear of tissue burning precludes the use of an emitter having that high power. One solution is to distribute the large optical power across multiple input sites, thereby bringing the total power to levels greater than 1 W without burning the tissue.

As an alternative, albeit no longer non-invasive method of illumination, a catheter can be threaded to the base of the brain. This catheter is then used as a source of light that is detected at the surface of the head.

Additional details regarding general considerations in DOT and other optical systems can be found in U.S. Pat. Nos. 5,853,370; 5,353,799; 5,421,329; 5,282,467; 5,782,237; 5,553,614; 5,792,051; 5,902,235; 5,795,292; 5,697,367; 5,584,296; 5,482,034; 5,477,853; 5,465,714; 5,217,013; 5,140,989; 5,139,025; 4,817,623; 4,768,516; 4,725,147; 4,570,638; and 5,779,631.

Use of Dyes for Enhancing DOT Imaging of Blood

For blood flow measurements using DOT, a bolus of dye (also called tracer or contrast agent) can be injected into the blood stream of the patient The injection is usually made intravenously and usually through the arm, taking about 1 second to complete. The bolus can be 1 to 10 ml (e.g., 5 ml) of dye. When a bolus of dye is introduced into the blood stream, the bolus travels relatively intact through the brain. As the bolus travels back through the heart and to the brain a second time, the bolus becomes dilute and spatially extended and diffuse. After several passes of the bolus through the heart (each cycle through the body taking about 20–40 seconds), it usually is no longer possible to recognize a spatially coherent contrast. By monitoring the first passage of the bolus through the brain, the amplitude of the detected light decreases as the bolus, which absorbs light, flows into the optically sampled volume of tissue. The amplitude then increases back to the baseline as the bolus flows out of the imaged region. The duration of this perturbation is a measure of blood flow, while the magnitude of the perturbation can serve as a measure of perfusion or blood volume. In addition, comparison of the onset and offset of the perturbation in different cortical regions of the brain can provide a relative measure of the blood transit time. All of these measures can serve to better characterize the state and evolution of a stroke by providing a spatial map or image of the abnormality in the brain over time.

For additional details regarding the use of a dye bolus in DOT, see Patel et al., Pediatric Research 43:34–39, 1998. A device suitable for multiple, automated bolus administrations is described in U.S. Pat. No. 5,722,956.

Useful dispersible chromophores include: drugs and dyes such as rifampin (red), -carotene (orange), tetracycline (yellow), indocyanine green (such as Cardio-Green®), Evan's blue, methylene blue; soluble inorganic salts such as copper sulfate (green or blue), $Cu(NH_3)^{2+}$ (dark blue), $MnO_4$ (purple), $NiCl_2$ (green), $CrO_4$ (yellow), $Cr_2O_7^{2-}$ (orange); proteins such as rhodopsin (purple and yellow forms) and green fluorescent protein (fluoresces green under blue light); and any of the Food and Drug Administration (FDA) approved dyes used commonly in foods, pharmaceutical preparations, medical devices, or cosmetics, such as the well-characterized non-toxic sodium salts FD&C Blue No. 1 (Brilliant Blue FCF), FD&C Green No. 3 (Fast Green FCF), FD&C Red No. 3 (Erythrosine), FD&C Red No. 40 (ALLURA® Red AC), FD&C Yellow No. 5 (Tartrazine), and FD&C Yellow No. 6 (Sunset Yellow FCF). Of these FD&C dyes, Yellow No. 5 is known to produce occasional allergic reactions.

Additional FDA approved dyes and colored drugs are described in the *Code of Federal Regulations* (CFR) for Food and Drugs (see Title 21 of CFR chapter 1, parts 1–99). The table below lists a number of suitable chromophores, their Chemical Abstract Service (CAS) Registration Numbers, colors, and absorption maxima.

| Chromophore | CAS Reg. No. | Color | Abs. Max. (nm) |
| --- | --- | --- | --- |
| Yellow No. 5 | 1934-21-0 | yellow | 428 |
| β-carotene | 7235-40-7 | orange | 466 |
| rifampin | 3292-46-1 | red | 475 |
| Yellow No. 6 | 2783-94-0 | yellow | 480 |
| tetracycline | 60-54-8 | yellow | N/A |
| Red No. 40 | 25956-16-6 | red | 502 |
| Red No. 3 | 16423-68-0 | red | 524 |
| Blue No. 2 | 860-22-0 | blue | 610 |
| Evan's Blue | 314-13-6 | blue | 610 |
| Green No. 3 | 2353-45-9 | green | 628 |
| Blue No. 1 | 2650-18-2 | blue | 630 |
| methylene blue | 7220-79-3 | blue | 668/609 |
| indocyanine green | 3599-32-4 | green | 800 (mostly IR) |

The dispersible chromophores listed above are generally (1) water-soluble at physiological pH, although fat-soluble chromophores (such as β-carotene) will also work if they are rapidly flushed from tissue, or (2) digestible or metabolizable through enzymatic pathways (such as methylene blue, which is rapidly metabolized by mitochondrial reductases, and proteins which are digested by proteases). In some cases, it may be possible to modify a chromophore to improve its dispersibility. A particular advantage of protein chromophores is that they can be conjugated to degradation inducing moieties, such as degradation signaling polypeptides using standard biochemical techniques. For example, green fluorescent protein can be conjugated to ubiquitin, which facilitates breakdown of the protein into small, invisible peptides by the eukaryotic ubiquitin proteolysis pathway.

Light Sources and Detectors of Scattered Light

There are numerous approaches for taking DOT measurements. In the simplest approach, a single optode delivers light to the scalp of an individual, and a single optode detects the scattered light. The optodes can be separated by 2.5 to 3.5 cm to maximize the detection of light that has traveled through the skull and into the cortex of the brain before returning to the detecting optode. For smaller optode separations, the detected light likely travels only through the skull. Larger optode separations result in smaller signal-to-noise ratios and a larger volume of tissue sampled, but have poor spatial resolution.

The 2.5 to 3.5 cm separation of emitters and detectors permits measurement of flow/mean transit time when a bolus moves through the position imaged by the pair of optodes. To diagnose and monitor the evolution of a stroke lesion, however, a spatial array of measurements are desirable. The array can provide measurements from region to region in the cortex, as well as the spatial extent (size) of any abnormality.

The wavelength of the light emitted from the optode should correspond to light that is detectably absorbed by the tissue or local blood to be imaged or that matches the absorption wavelength of a fluorescent or non-fluorescent dye. In the case of blood, a bolus of dye can be injected into the patient as described above and used to enhance the absorption of light by the blood in a time-dependent manner. For example, if a bolus of indocyanine green is injected into a patient for DOT, an appropriate wavelength for the light emitted by the optode is 780–800 nm, the peak absorption wavelength of indocyanine green.

The optodes (light sources and detectors) can be positioned on a patient's head using any means known in the art. For example, a stiff helmet made of Styrofoam and having holes in various positions around its hemisphere can be used to group, position, and fix the optodes against an individual's scalp.

Figure 16A:
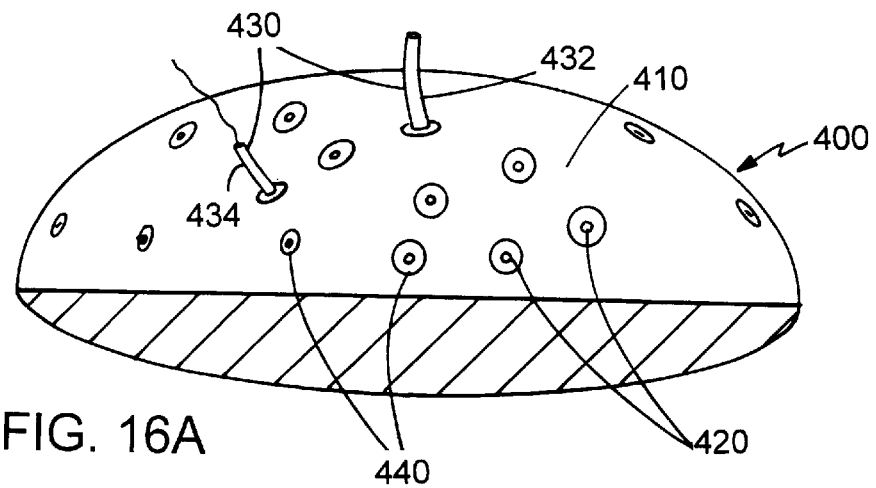
FIGS. 16A–16C are diagrams of a scalp cap for use in the methods of the invention.
Figure 16B:
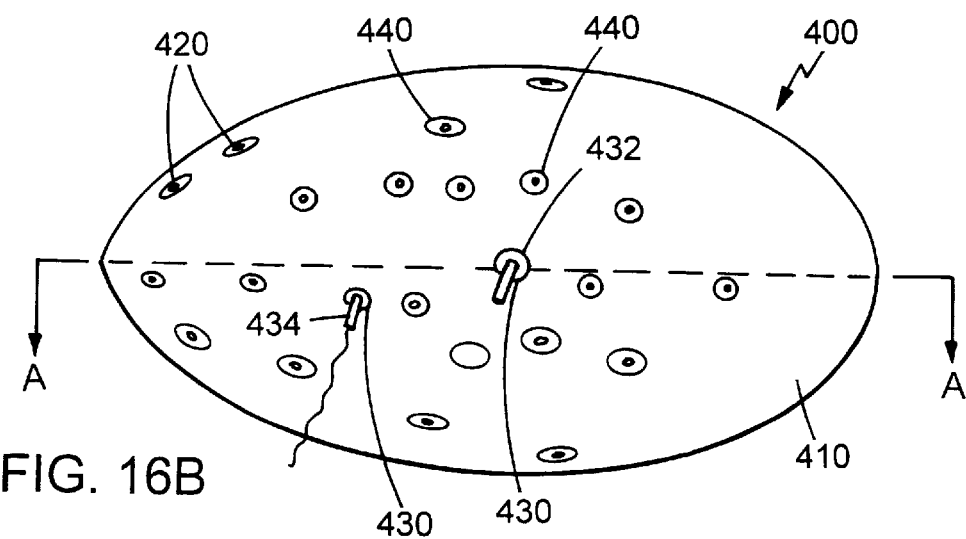
Figure 16C:
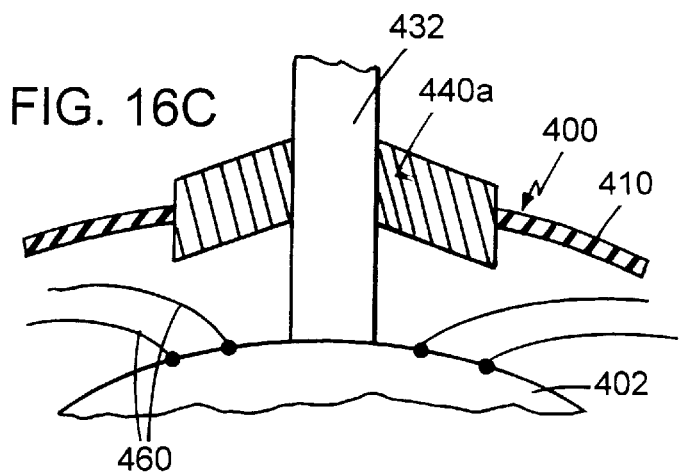

Alternatively, a flexible and elastic cap made of rubber or nylon or the like, similar to a swimmer's cap, can be used to arrange the optodes. Referring to FIGS. 16A–16C, a device 400 is formed from a flexible, elastic cap 410 containing holes 420 for placement of a plurality of optodes 430, only two of which are shown in FIGS. 16A and 16B. The flexible and elastic nature of the cap helps ensure a fixed, tight fit over an individual's head. The two optodes shown include an optical fiber 432, which delivers light from a laser (not shown) to scalp surface 402, and a photodetector 434 for detecting scattered light. All optodes 430 are flexibly attached to cap 410 by rubber grommets 440. When cap 410 is tightly fitted over the head, optodes 430 are pressed against scalp surface 402, with pressure generated by displacement of rubber grommets 440, such as displaced rubber grommet 440a (see FIG. 16C). To eliminate signal artifacts from hair shafts 460 interposed between scalp surface 402 and optodes 430, device 400 can be shifted back and forth while cap 410 is placed over scalp surface 402. This shifting movement causes, for example, optode 432 to move hair fibers 460 away from the scalp area in contact with optical fiber 432 (see FIG. 16C). Other similar arrangements and devices (e.g., caps or helmets) are suitable for use in the methods of the invention.

In certain contexts, it is desirable to emit and detect light of two different wavelengths. A second wavelength is useful, for example, to determine the degree of oxygenation (relative amount of oxyhemoglobin) of the blood, while the first wavelength is used to detect the concentration of a dye introduced into the blood stream of a subject as described herein. Monitoring scattered light of the second wavelength can also help calibrate the measurement of dye concentration in blood by accounting for variations in the signals at the first wavelength as a result of changes in blood oxygenation.

Circuitry for Detection of Scattered Light

A suitable circuitry for resolving small difference in light intensity returning to one or more optode from the brain is shown in FIG. 1. The circuit enables the use of two wavelengths, though only one wavelength is required for the methods of the invention. For example, a single wavelength of 780 nm would be appropriate when detecting a bolus of indocyanine green passing through the vasculature of the brain. The use of two wavelengths enables more than one dye to be used, each dye having a different absorption and/or fluorescent wavelength. The two dyes then offer collaborating signals that provide more reliable detection of bleeds or ischemic events. Further details regarding such benefits are discusses elsewhere herein.

The phase encoding shown in the circuit of FIG. 1 can spatially distinguish light emitted into the head from sources at different locations (e.g., at 5 to 25 locations, particularly at 18 locations) or at the same location but with different wavelengths. This ability is important if the optodes are to be powered continuously to fully resolve the passage of a bolus. In other words, a prototype DOT imager having only one light source can only energize one source at a time, which limits the data acquisition rate. A more efficient technique, using the above circuit, is to exploit the phase diversity afforded by coherent detection by modulating each laser wavelength at the same 2 kHz frequency but in phase quadrature with each other. Double-balanced mixers are insensitive to coherent signals which arrive exactly 90° out of phase with the demodulation clock. When a quadrature signal passes through the mixer, the DC level of the resulting signal averages out to zero, similar to uncorrelated noise. The mixer, fed by a detector signal containing both in-phase and quadrature components (generated by the two laser sources), will demodulate the in-phase signal only, and will completely ignore the quadrature component. The same holds true for the second mixer, fed with a "quadrature" demodulation clock. Double-pole post-detection filters are used to attenuate the strong second harmonic component produced by the quadrature source. This use of phase-encoding allows us to sample two sources simultaneously.

The circuit 20 shown in FIG. 1 is such a quadrature encoded system, as described immediately above, that places the signals from the two source wavelengths into mutually orthogonal phases at one carrier frequency, centered at about 2 kHz. The electrical signals representing the intensity of each source wavelength are extracted from the single detector channel using synchronous or phase-sensitive detection. The 7555 microprocessor 22 serves as the master clock, which is divided down and split into I and Q (in-phase and quadrature, respectively) outputs 24 and 26. The I and Q outputs 24 and 26 are then used to directly modulate the bias current through the two-laser diode sources 28 and 30, respectively. Since the received signals will experience a slight but significant propagation delay through the detector, the demodulator clocks are delayed by the exact same amount using adjustable R-C phase shifters 24a and 26a. The pots are adjusted to maximize the signal level of the main component while nulling the quadrature component to zero. The output of the double-balanced mixers 34 and 36 are then separated by the two-stage lowpass filters 38 and 40 to remove any AC components, and buffered through output buffers 42 and 44, yielding the two synchronously rectified DC signals, "I" output (46) and "Q" output (48).

Figure 2:
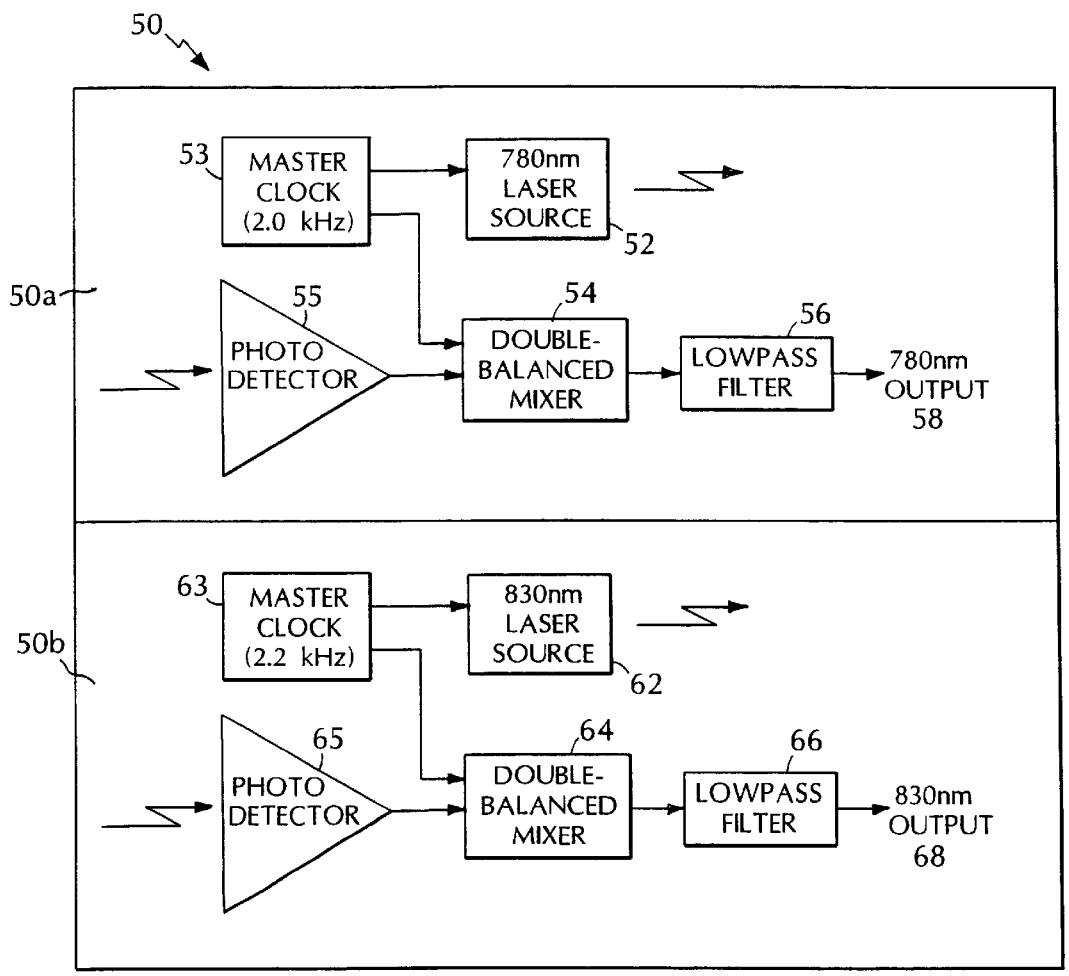

Another approach for energizing and distinguishing multiple sources simultaneously is to encode different emitting optodes with different modulation frequencies. A schematic of such a system is shown in FIG. 2. The frequency encoded system 50 operates in a manner similar to the circuit 20 shown in FIG. 1, except that each source wavelength 52 and 62 is modulated and demodulated at its own unique frequency. This is essentially the equivalent of two separate single-channel subsystems 50a and 50b operating independently. Each master clock operates at a slightly different frequency. The frequencies must differ by at least three times the baseband (post-detection) bandwidth and should not be within the same distance of any of the frequency harmonics to avoid interchannel cross-talk.

Subsystems 50a and 50b are nearly identical and contain components that operate as described above. Subsystem 50a synchronizes a 780 nm laser source 52 with a photo detector 55 using a 2 kHz masterclock 53, in order to improve the signal-to-noise ratio of the detected signal. The signal from photodetector 55 passes through a double-balanced mixer 54, to demodulate the 2 kHz carrier signal to a DC level, before separation by a lowpass filter 56, yielding output 58. Similarly, subsystem 50b synchronizes a 830 nm laser source 62 with a photo detector 65 using a 2.2 kHz masterclock 63. The signal from photodetector 65 passes through a double-balanced mixer 64 before separation by a lowpass filter 66, yielding output 68.

Figure 3:
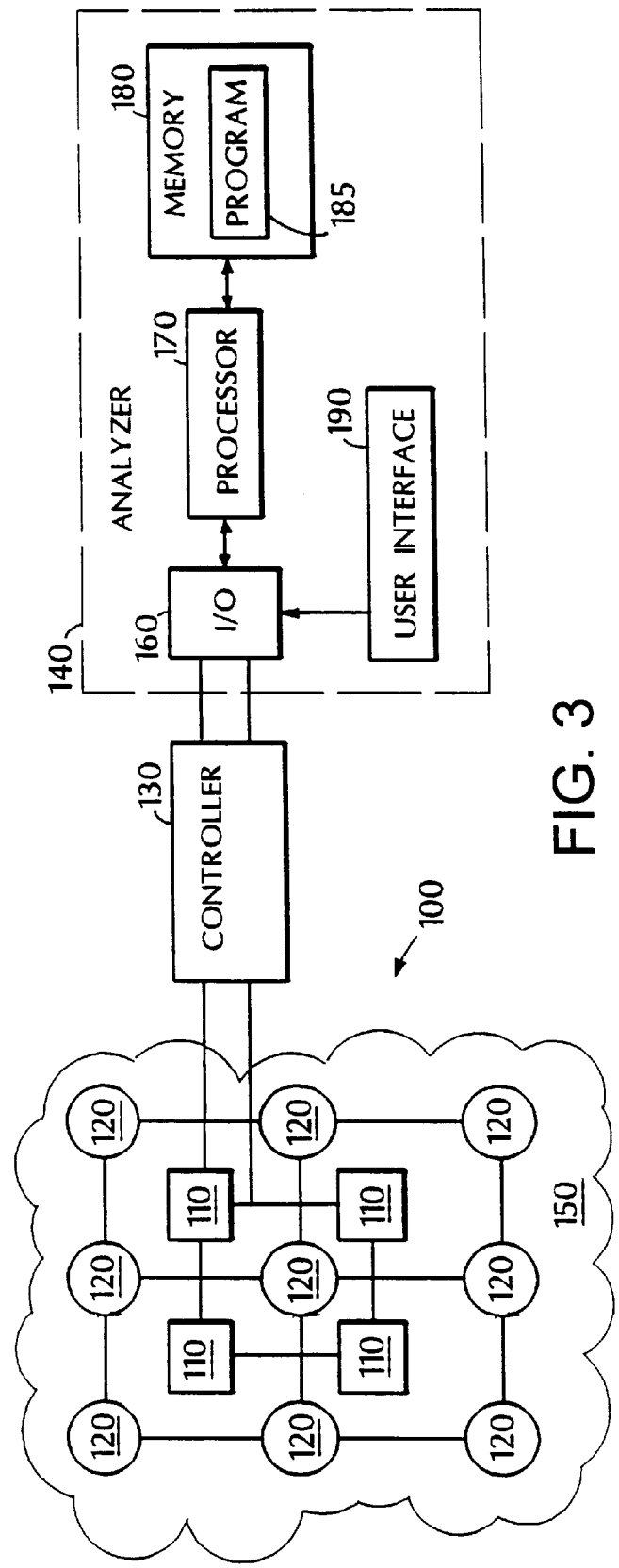

A schematic diagram of a DOT array system is shown in FIG. 3. The system 100 includes an array of spatially separated light sources 110 and spatially separated detectors 120. During use, the array of sources and detectors is positioned over a sample 150 to be imaged, e.g., a patient's head to image blood within the brain. A controller 130 connected to light sources 110 sequentially triggers them to couple light into sample 150, which is a highly scattering media (e.g., blood and brain tissue) that causes the light to become diffuse within the sample. For each sequentially triggered source, each detector 120 measures the light that reaches it through sample 150. Controller 130 is also connected to detectors 120 and selectively channels the signals from the detectors. An analyzer 140 is connected to controller 130 and analyzes the signals measured by detectors 120.

The signal g(i,j) measured by the $j^{th}$ detector in response to light coupled into the sample by the $i^{th}$ source can be expressed as:

$$g(i,j) = S^i D^j f(i,j) \tag{1}$$

where f(i,j) is the transmittance of the sample from the $i^{th}$ source to the $j^{th}$ detector, and $S^i$ and $D^j$ are coupling coefficients for the $i^{th}$ source to the $j^{th}$ detector, respectively. The transmittance f(i,j) depends only on the optical properties, e.g., the spatially varying absorption and scattering coefficients, and can be numerically calculated by a forward calculation if the optical properties are known. Conversely, if the transmittance f(i,j) can be calculated from the measured signals g(i,j), an inverse calculation can be performed on f(i,j) to yield the optical properties of the sample (e.g., a brain) and reveal, e.g., the presence of an object (e.g., blood flowing through a blood vessel) hidden in the sample (e.g., a brain). The source coupling coefficient $S^i$ includes all of the factors associated with coupling light generated from the $i^{th}$ source into the sample. The detector coupling coefficient $D^j$ includes all of the factors associated with coupling light out of the sample to generate an output signal at the $j^{th}$ detector.

Figure 4:
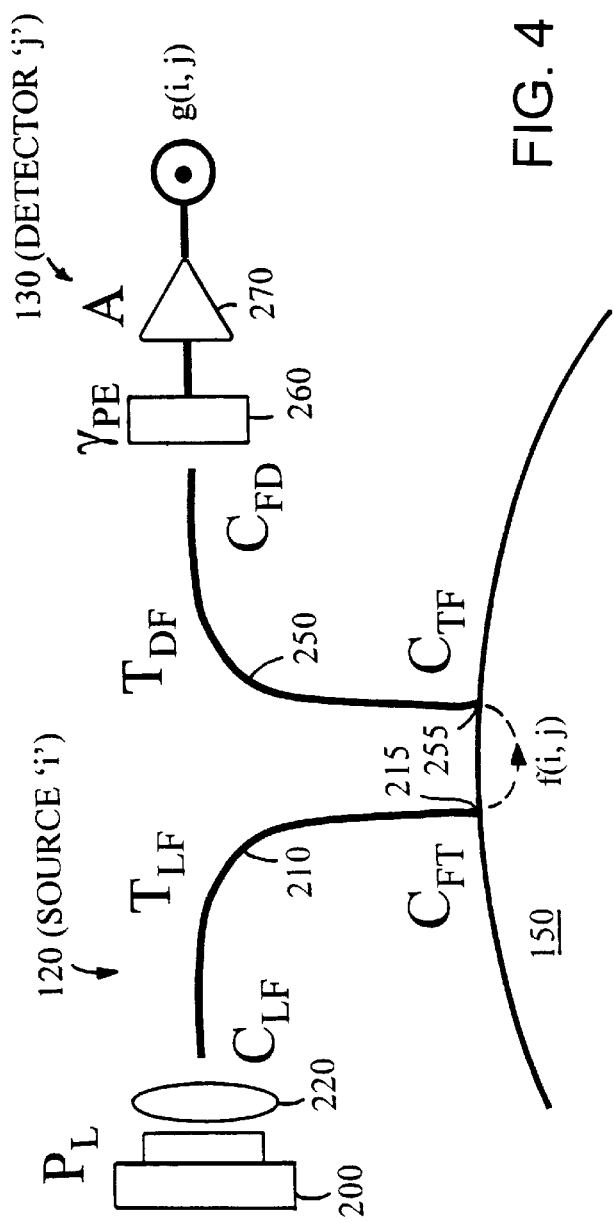
FIG. 4 is a schematic diagram of a source-detector pair for the system shown in FIG. 3.

For example, in one embodiment shown in FIG. 4, each source 120, e.g., the $i^{th}$ source, includes a diode laser 200 for producing the optical radiation, an optical fiber 210, and a lens 220 for coupling the optical radiation into fiber 210, which includes an end 215 adjacent sample 150 for directing the optical radiation into the sample. Each detector 130, e.g., the $j^{th}$ detector, includes an optical fiber 250 having an end 255 adjacent sample 150 for receiving the optical radiation emitted from sample 150, a photodetector 260 for measuring the intensity of the optical radiation received by fiber 250, and an amplifier 270 for amplifying the output of photodetector 260 to give the measured signal g(i,j). In this embodiment, the source coupling coefficient $S^i$ is the product of the fluence $P_L$ produced by diode laser 200, the coupling coefficient $C_{LF}$ of the lens 220 to the fiber 210, the transmission coefficient $T_{LF}$ of fiber 210, and the coupling coefficient $C_{FT}$ at the interface of fiber 210 and sample 150. Similarly, the detector coupling coefficient $D^j$ is the product of the coupling coefficient $C_{TF}$ at the interface of fiber 250 and sample 150, the transmission coefficient $T_{LF}$ of fiber 260, and the coupling coefficient of the sample fluence produced by the diode laser $P_L$, the coupling coefficient $C_{FD}$ between fiber 260 and photodetector 260, the efficiency $\gamma_{PE}$ of photodetector 260, and the gain A of amplifier 270.

In other embodiments, the light source can include a laser other than a diode laser, e.g., an ultrafast laser, or instead it can include an incoherent source. Also, the sources can include a common light source that selectively couples light into one of multiple fibers that deliver the light to spatially separated locations on the sample. Alternatively, the sources need not include optical fibers at all. For example, the lasers themselves can be positioned adjacent the sample or can include beam delivery optics to direct the light to the sample through free space. However, this method does not remove the blood from the scalp as described above. Furthermore, the light sources can provide light at multiple wavelengths by including, e.g., multiple diode lasers.

Calibration Issues

Calibration of signals generated from the methods of the invention can be performed using any means in the art, as well as using the new calibration methods described below. In general, the relationship between absorption and concentration of a natural tracer, such as oxyhemoglobin, is described by the Beer-Lambert law and modified versions thereof. The calculation of cerebral blood flow from the concentration of tracer is based on the Fick principle, which states that the rate of accumulation (Q) of tracer in the organ of interest is equal to the difference between the rate of arrival and the rate of departure of the tracer. Assuming that the time that the time taken to inject the tracer bolus is by comparison relatively short enough to ignore, a measurement of the amount accumulated in an organ can be made at a specific time t (if inducing the tracer at time 0), provided that t is less than the minimum transit time through the organ, i.e., no tracer would be leaving the organ. Then the accumulation of tracer (Q) can be expressed as:

$$Q(t) = \int_0^t F \cdot C_a dt \qquad (A),$$

where $C_a$ is the arterial concentration of tracer. When flow F is constant, the Eq. (A) can be derived as:

$$F = Q(t) / \int_0^t C_a dt \qquad (B).$$

For example, blood flow measurements can be made by near-infrared spectroscopy (NIRS) using oxyhemoglobin as tracer in transmittance mode as described in Edwards et al., J. Appl. Physiol. 75:1885–1889, 1993. The experiment described in the reference immediately above was performed in the forearms of six healthy young adults. For comparison, blood flow was also measured by venous occlusion plethysmography, and the relation between flow calculated by NIRS (y) and plethysmography (x) was y=0.93x+0.30. Calculation of the signals generated by the methods of the invention can be similarly performed. Cerebral blood flow can also be measured using the calculations employed in Skov et al., Pediatr. Res. 30:570–573, 1991; Bucher et al., Pediatr. Res. 33:56–60, 1993; Fallon et al., Ann. Thorac. Surg. 56:1473–1477, 1993; and Elwell et al., J. Appl. Physiol. 77:2753–2760, 1994. In addition, tracer dyes can be used as a more flexible alternative to oxyhemoglobin in NIRS. Measurements using the dye ICG can produce a relatively high signal-to-noise (S/N) ratio than when using oxyhemoglobin as tracer. See, e.g., Patel et al., supra.

However, many of the past studies do not show that optical methods utilizing a tracer can be used to quantify cerebral blood flow (CBF), despite their calibration methods. At best, they show that a flow index can be measured that is proportional to the real flow, but that the proportionality constant varies from study to study. This indicates that the proportionality constant depends on the experimental design. Eq. (A) shows that flow F is equal to the concentration of a tracer measured at a given time Q(t) divided by the integrated arterial concentration $C_a(t)$ feeding into the organ of interest. Thus, an accurate quantitative measure of F requires a quantitative measure of Q(t) and $C_a(t)$. This requires absolute quantification of the absorption coefficient from the optical measurements, since the concentration and absorption coefficient are linearly related through the extinction coefficient of the tracer. If the tracer were uniformly distributed throughout the tissue sampled by the diffusing light, then this would be a simple task. However, in the case of analyzing the CBF, the tracer has different concentrations in the scalp, skull, and brain. Quantification of tracer concentration in this case can be done by imaging. To make the situation worse, the tracer is not uniformly distributed in each tissue type as it is localized to blood vessels which comprise ~5% of the tissue. Thus, assuming no saturation of the optical signal by the tracer, one needs to know the volume fraction of the blood vessels in order to quantify the tracer concentration. However, this is not likely to be sufficient since saturation easily occurs with ICG as the tracer, since the dye increases the absorption coefficient of the blood vessels such that the sensitivity of detection of the blood vessels drops relative to the surrounding tissue matrix. All of these factors introduce systematic errors rendering an absolute measurement of CBF difficult to achieve. Further, a relative measurement of CBF is not likely to be accurate since these factors change from patient to patient, and can also change within a patient from measurement to measurement.

Our solution, therefore, is to self-calibrate the measured flow index in abnormal tissue (stroke) against normal tissue. The ratio of these flow indices will nearly equal the ratio of the true flow in each region since the systematic errors will nearly cancel in the ratio. This new method is described below.

Other than the circuitry considerations discussed above, the signals still must be calibrated correctly. To analyze the measured values g(i,j) discussed above, a calibration is required to convert the measured values for g(i,j) into the transmittance values f(i,j). According to Equation (1), this requires a calibration for the value of $S^i D^j$ for every source-detector pair. As will be described below, analyzer 140 determines self-consistent values for $S^i D^j$ based on the set of measured values g(i,j) and the results of a numerical calculation for f(i,j) corresponding to an approximate model of the sample. Once the calibration is determined, the same set of measured values g(i,j) can be used to calculate f(i,j) according to Equation (1), from which the analyzer can perform the inverse calculation. Because the same set of measured values are used for the calibration and the inverse calculation, the optical properties determined by the analyzer do not include systematic errors caused by fluctuations in the source and detector coupling coefficients.

In the description that follows, it is assumed that the sources provide continuous wave (CW) optical radiation and the detectors measure the intensity of the optical radiation, in which case $g(i,j)$, $f(i,j)$, $S^i$, and $D^j$ are all real-valued. However, the calibration techniques described herein can also be applied to other diffuse optical measurement techniques in which the sources do not provide CW radiation. For example, in some techniques, the amplitude of the optical radiation provided by the source is modulated to create photon density waves in the sample, and the detectors are configured to measure the amplitude and phase of the photon density waves after propagation through the sample. In this case the values for $g(i,j)$, $f(i,j)$, $S^i$, and $D^j$ can be complex. For a general reference on DOT with modulated optical radiation see, e.g., O'Leary et al., Phys. Rev. Lett. 69: 2658, 1992. Furthermore, in other techniques, each source provides a temporally coherent light pulse, e.g., a picosecond pulse, and the detectors are time-gated to measure the temporal delay of the diffuse light pulse in addition to its intensity. For a general reference on such time-domain DOT techniques, see, e.g., Patterson et al., Appl. Opt. 28: 2331, 1989; and Arridge, Inverse Problems 15:R41–R93, 1999.

Calibration Method

Assuming $N_s$ sources and $N_d$ detectors and following Equation (1) above, the coupling coefficient of the $i^{th}$ source and $j^{th}$ detector can be expressed as:

$$S^i = \frac{1}{N_d} \sum_{j=1}^{N_d} \frac{g(i,j)}{f(i,j) \cdot D^j}, \tag{2}$$

$$D^j = \frac{1}{N_s} \sum_{i=1}^{N_s} \frac{g(i,j)}{f(i,j) \cdot S^i}, \tag{3}$$

$$S^i D^j = \frac{g(i,j)}{f(i,j)}. \tag{4}$$

Equation (2) is the average of all measurements made with source i and Equation (3) is the average of all measurements made with detector j. Substituting Equations (3) and (4) into Equation (2) we obtain a relationship between the source coupling coefficient $S^i$ and the detector coupling coefficient $D^k$, corresponding to the $i^{th}$ source and the $k^{th}$ detector, respectively:

$$S^i = \frac{N_s}{N_d} \sum_{j=1}^{N_d} \frac{g(i,j)}{f(i,j) \cdot \sum_{ii=1}^{N_s} \frac{g(ii,j)}{f(ii,j)} \cdot \frac{f(ii,k)}{g(ii,k)} \cdot D^k} = \frac{A_s^{ik}}{D^k}, \tag{5}$$

and likewise between $D^j$ and $S^l$, corresponding to the source and detector coupling coefficients for the $j^{th}$ detector and the $l^{th}$ source, respectively:

$$D^j = \frac{N_d}{N_s} \sum_{i=1}^{N_s} \frac{g(i,j)}{f(i,j) \cdot \sum_{jj=1}^{N_d} \frac{g(i,jj)}{f(i,jj)} \cdot \frac{f(l,jj)}{g(l,jj)} \cdot S^l} = \frac{A_d^{jl}}{S^l}. \tag{6}$$

Thus, $$S^i D^j = \frac{L(i,j,k,l)}{S^l D^k}, \tag{7}$$

where $$L(i,j,k,l) = A_s^{ik} A_d^{jl} \tag{8}.$$

Note that $L(i,j,k,l)$ is a function only of the number of sources and detectors, $N_s$ and $N_d$, the measurements, $g(i,j)$, and the optical properties of the medium as reflected through $f(i,j)$. In other words, $L(i,j,k,l)$ is not dependent on the coupling coefficients.

Combining Equations (2), (3), and (7), the coupling coefficient product $S^l D^k$ must minimize the following expression to be consistent with each other and with the measurements $g(i,j)$:

$$F(S^l D^k) = \sum_{i=1}^{N_s} \sum_{j=1}^{N_d} \left( \frac{L(i,j,k,l)}{S^l D^k} f(i,j) - g(i,j) \right)^2. \tag{8}$$

Assuming that $f(i,j)$ can be calculated from an approximate model, the value for $S^l D^k$ can be calculated by minimizing Equation (9) with respect to $S^l D^k$. The minimization can be repeated for every source-detector pair, or alternatively, once the value for $S^l D^k$ is determined for the l-k source-detector pair, the other coupling coefficient products can be determined from Equation (7). Although the calibration is non-linear, with no unique solution for the individual coupling coefficients $S^i$ and $D^j$, an exact solution exists for the coupling coefficient product of every source-detector pair, which is all that is needed for the calibration. The minimization of Equation (9) can be performed using standard techniques known in the art, see, e.g., Press et al. in *Numerical Recipes in C: The Art of Scientific Computing* (Cambridge U. Press, New York, 1988).

To perform the minimization in Equation (9), analyzer 140 makes a numerical forward calculation for $f(i,j)$ based on an approximate model of the sample. An initial model can be that the sample is homogenous with a constant absorption coefficient $\mu_a$ and a constant reduced scattering coefficient $\mu'_s$. Once the calibration is performed, an inverse calculation can provide perturbative corrections to the model to show spatial variations in the optical properties of the sample. Numerical techniques for the forward and inverse calculations are known in the art and will be briefly described in the next section. However, for the simple case of an infinite homogeneous sample, the model forward calculation simplifies to the following expression:

$$f(i,j) = \frac{3\mu'_s}{4\pi |r_{ij}|} \exp\left[-(3\mu'_s \mu_a)^{\frac{1}{2}} |r_{ij}|\right], \tag{10}$$

where $|r_{ij}|$ is the distance between the $i^{th}$ source and the $j^{th}$ detector on the sample surface.

If the background optical properties are not known, then an iterative procedure can be used to find $\mu_a$, $\mu'_s$, and the coupling coefficients. The procedure involves estimating $\mu_a$ and $\mu'_s$ to calculate $f(i,j)$, and then minimizing $F(S^l D^k)$ in Equation (9) to find the coupling coefficient $S^l D^k$. The procedure is repeated with different values of $\mu_a$ and $\mu'_s$ to minimize $F(\mu_a, \mu'_s, S^l D^k)$ with respect to all three parameters. For spectroscopic applications where constant values of $\mu_a$ and $\mu'_s$ are expected over the spatial extent of the measurement, the technique provides an accurate determination of the absolute values of $\mu_a$ and $\mu'_s$.

Once all of the coupling coefficients $S^iD^j$ are determined based on the initial model calculation, experimental values for f(i,j) are calculated from Equation (1) based on the determined coupling coefficients and the measurements g(i,j). The analyzer then performs an inverse calculation on the experimental values for f(i,j) to determine perturbations to the homogeneous model for the sample. If necessary, the calibration can be repeated for an improved model of the sample based on the results of the inverse calculation. In turn, the inverse calculation can be repeated for experimental values f(i,j) calculated from Equation (1) using the revised calibration. This iterative process can be repeated until the results for the spatially varying optical properties of the sample begin to converge.

Figure 5:
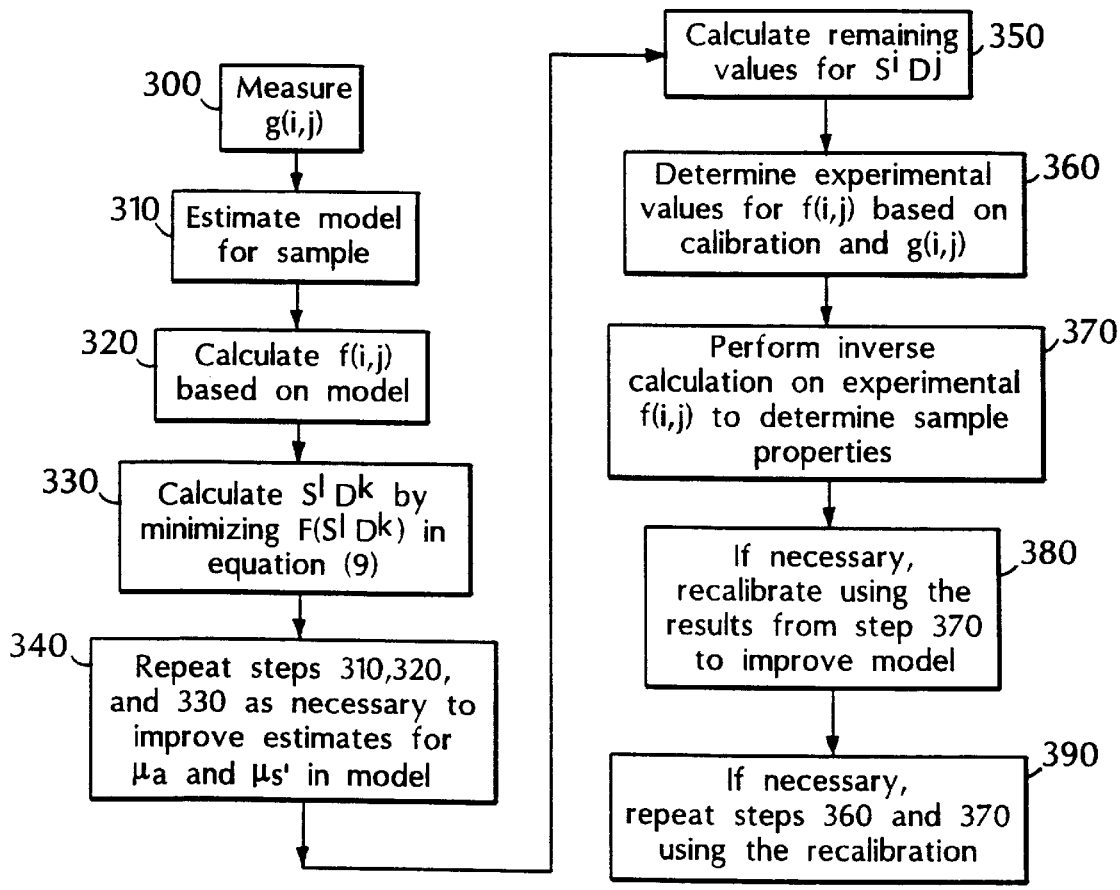
FIG. 5 is a flow chart summarizing the steps of one embodiment of the calibration method described herein.

The steps performed by the analyzer to carry out the calibration and analysis of measurements g(i,j) for imaging applications is summarized by the flow chart in FIG. 5.

In step 300, the analyzer receives measured signals g(i,j) from the detectors.

In step 310, an initial model for the sample is input into the analyzer, for example, the initial model may treat the sample as being homogeneous. In this case, values for $\mu_a$ and $\mu'_s$ are estimated if they are otherwise unknown.

In step 320, the analyzer calculates values for f(i,j) based on the sample model and a forward calculation. For example, if the sample is modeled to be homogeneous and infinite, Equation (10) can be used.

In step 330, the coupling coefficient $S^iD^k$ is determined by minimizing $F(S^iD^k)$ with respect to $S^iD^k$ in Equation (9), the other parameters in Equation (9) being specified by the measurements for g(i,j) and the values for f(i,j) from the model forward calculation in step 320.

In step 340, steps 310–330 are repeated as necessary with additional estimates for $\mu_a$ and $\mu'_s$, until values are found for $S^iD^k$, $\mu_a$, and $\mu'_s$ that optimally minimize $F(S^iD^k)$.

In step 350, the values for all of the remaining coupling coefficients $S^iD^j$ are determined by either: 1) calculating $S^iD^j$ using Equation (7) and the value for $S^iD^k$ determined in step 340; or 2) replacing the argument $S^iD^k$ for F in Equation (9) with the coupling coefficients $S^iD^j$ corresponding to each of the remaining source-detector and determining the value $S^iD^j$ that minimizes F.

In step 360, the calibration coefficients $S^iD^j$ determined in steps 340 and 350, and the measurements g(i,j) from step 300 are used to calculate experimental values for f(i,j) based on Equation (1).

In step 370, an inverse calculation is performed on the variation of the experimental values for j(i,j) from the expected values for a homogeneous medium calculated in step 360 to determine spatial variations in the optical properties of the sample, e.g., an object hidden with a highly scattering sample.

In step 380, if necessary, the model for the sample estimated in step 310 is revised based on the results from step 370, then steps 320, 330, and 350 are repeated, one time, to recalculate the calibration coefficients $S^iD^j$ based on the revised sample model.

In step 390, if necessary, steps 360–370 are repeated, one time, using the recalculated calibration coefficients from step 380 to improve the determination of the spatial variations in the optical properties of the sample. Steps 380–390 can be iteratively repeated as necessary until the spatially varying optical properties determined in step 390 converge to within a desired accuracy.

For spectroscopic applications in which the optical properties of the sample are expected to be homogeneous, the method can be terminated at step 340 because the calibration technique provides direct determination of the absolute values of $\mu_a$, and $\mu'_s$.

Also, in other embodiments, the summations in the Equations above need not be over every source and detector in the experimental apparatus. For example, source-detector measurements between any two sources and any two detectors are sufficient to determine all of the source-detector coupling coefficient products corresponding to that set of sources and detectors. This example would be equivalent to setting $N_s=2$ and $N_d=2$ in the above Equations. Once some of the coupling coefficient products are determined based on a subset of all possible source-detector measurements, the remaining coupling coefficient products can be determined with relatively fewer additional measurements.

Forward and Inverse Calculations

Techniques for the forward and inverse calculations of light propagation within the sample are known in the art. See, e.g., Arridge, supra. An exemplary formulation of the calculation is described below.

The absorption coefficient $\mu_a$ and diffusion coefficients D, where $D=v/[3(\mu_a+\mu'_s)]$, are expanded into a spatially independent background term $\mu_a^o$ and $D_o$, respectively, and a perturbative spatially dependent terms $\delta\mu_a(r)$ and $\delta D(r)$, respectively. These terms are then incorporated into the diffusion equation, whose formal solution can be expressed as an integral equation by use of the appropriate Green function corresponding to the sample's boundary conditions.

In the present case, the light energy density is expanded in a perturbative series, i.e., $U(r)=U_0(r)+U_1(r)+\ldots$, and solved to first order. The first-order perturbative solution to the heterogeneous equation, in the limit in which $U_1$ far less than $U_0$, is given by:

$$U_0(r_s, r_d) = M\exp(ik_0|r_s - r_d|)/(4\pi D_0|r_s - r_d|) \quad (11)$$

$$U_1(r_s, r_d) = \int_V \left[-\delta\mu_a(r)vD_0^{-1}U_0(r_s, r)G(r, r_d) + \frac{\delta D(r)}{D_0}\nabla U_0(r_s, r) \cdot \nabla G(r, r_d)\right] d^3r \quad (12)$$

where M is the amplitude of the source located at $r_s$, $G(r,r_d)$ is the Green function solution of the homogeneous equation at detector position $r_d$, v is the speed of light in the medium, and $k_0=[(-v\mu_a^o+i\omega)/D_o]^{1/2}$ is the photon density wave number, where $\omega$ is the source modulation angular frequency. If an infinite medium is assumed, the Green function is $G(r,r_d)=\exp(ik_0|r-r_d|)/(4\pi|r-r_d|)$. The integral in Equation (12) is over the entire sample volume. In the embodiment described above, the source is a CW source without any modulation. Thus, $\omega$ goes to zero and $k_0$ is purely imaginary, so that both $U_0(r)$ and $U_1(r)$ are real-valued. The first term in the integral of Equation (12) corresponds to absorbing inhomogeneities, whereas the second term corresponds to scattering inhomogeneities. Where it is known that one or other type of inhomogeneity dominates, the non-dominant term can be dropped from Equation (12).

Based on Equations (11) and (12), the forward calculation corresponds to:

$$f(i, j) = \frac{U_0(r_s^{(i)}, r_d^{(j)}) + U_1(r_s^{(i)}, r_d^{(j)})}{M}. \quad (13)$$

In other embodiments, it is also possible to expand the perturbation series beyond the first term.

For the image reconstruction, i.e., the inverse calculation, the integral in Equation (12) is digitized into a sum over voxels (i.e., volume elements), and equated to a series of the values for $U_1$ $(r_s^{(i)}, r_d^{(j)})$, which is extracted from the measurements g(i,j) and the calibration. This yields a set of coupled linear equations that relates to the values of $\delta\mu_a$ and $\delta D$ in each voxel within the sample, which correspond to spatial variations in $\mu_a$ and $\mu_s$. Many numerical methods are available for solving this system of equations including, for example, Simultaneous Iterative Reconstruction Technique (SIRT) and single value decomposition (SVD). For a reference on SIRT, see, e.g., Kak et al., in *Principles of Computerized Tomographic Imagin*, (IEEE, New York, 1988), Chap. 6, p. 211. For a reference on SVD, see, e.g., Press et al., supra, at Chap. 2, p. 52.

Software Implementation

The calibration method can be implemented in hardware or software, or a combination of both. The method can be implemented in computer programs using standard programming techniques following the method and figures described herein. Program code is applied to input data to perform the functions described herein and generate output information. The output information is applied to one or more output devices such as a display monitor.

Each program is preferably implemented in a high level procedural or object oriented programming language to communicate with a computer system. However, the programs can be implemented in assembly or machine language, if desired. In any case, the language can be a compiled or interpreted language.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The calibration method can also be implemented as a computer-readable storage medium, configured with a computer program, where the storage medium so configured causes a computer to operate in a specific and predefined manner to perform the functions described herein.

For example, referring again to FIG. 3, analyzer 140 includes a processor 170, and input/output control card 160, a user interface 190 such as a keyboard and monitor, and a memory 180. The memory stores a program 185 specifying the steps of the calibration method. When executed, the program causes the processor to carry out the steps of the calibration method.

Additional details regarding the calibration method immediately above are described in U.S. Provisional Application Ser. No. 60/154,423, filed Sep. 17, 1999.

Once the signals have been calibrated and sorted, indicating changes, if any, in the scattered light at each individual location, the separate data points at each position can be assembled into an image, which is then conveyed via a visual display. The displayed image can indicate an actual or modeled outline of a tissue or organ, with a region of abnormality indicated by a different color or shade of gray. Alternatively, the spatial abnormality can be indicated by a rough outline (e.g., a box) of the affected region, with a caption of text stating the nature of the abnormality (e.g., increased blood volume or delayed blood flow). Other techniques for displaying images containing target structures such as abnormalities are also suitable for use in the invention.

Figure 6A:
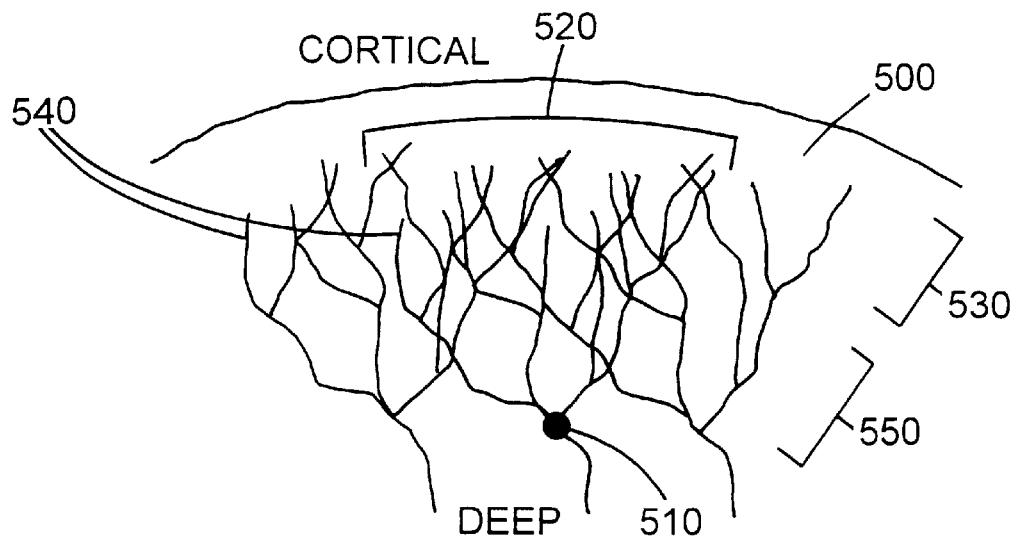
FIGS. 6A and 6B are schematic diagrams of blood vessels in a brain with a cortical ischemic event (FIG. 6A) and a brain with a deep ischemic event (FIG. 6B).
Figure 6B:
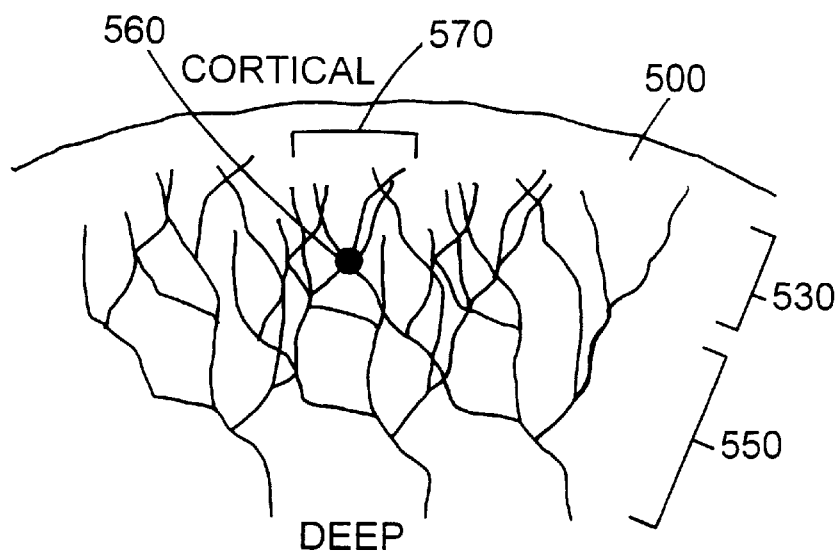

Distinguishing a Cortical Ischemic Event from a Deep Ischemic Event in the Brain It is possible to distinguish sub-cortical from cortical lesions through their hemodynamic spatio-temporal signa-tures (see Example 2 below). For instance, a sub-cortical lesion is likely to induce a broad spatial and temporal hemodynamic variation within the cortex. To illustrate the phenomenon, one must first note that major arteries feeding the brain enter at the organ's center. Blood then flows towards the cortex via branching arterioles (FIGS. 6A and 6B). In general, however, each portion of the cortex is fed by more than one set of arterioles and associated capillaries, an architecture that many believe evolved to minimize tissue damage when an ischemic event occurs deep in the brain.

Thus, an ischemic event deep in the brain will not completely shut off the flow of blood to a cortical region. Instead, referring to FIG. 6A, an ischemic event 510 in a deep portion 550 leads to a diffuse, affected region 520 of decreased and delayed blood flow to cortical portion 530 of a brain 500 due to a longer vessel path taken by the blood in arterioles 540. In addition, collateral blood flow will mix tracer from unaffected brain tissue with blood that contains little tracer because of the ischemia, resulting in a less pronounced dilution of the tracer than seen immediately downstream of the ischemic event. This is analogous to cars detouring around a major accident on a highway by exiting the highway, taking back roads (collateral arterioles) and thereby affecting cars headed to other destinations (other regions of the cortex), then re-entering the highway to reach their destination. The detoured cars arrive at their faraway destination (the cortex of the brain) later than would have been expected and cause cars traveling elsewhere to be delayed as well.

In contrast, referring to FIG. 6B, a cortical lesion 560 in brain 500 causes a more localized, affected region 570 in cortical portion 530 that exhibits a delay in the transit of a tracer compound as well as a greater reduction in the quantity of the tracer that moves through local region 570. Referring to the car analogy above, if a major accident on the highway occurred just before the destination, an observer would (1) see few cars making it to the destination because there are no exits to leave the highway; and (2) little effect on other cars using other highways because the detoured cars, if they can exit the highway at all, only need to travel a short distance to their destination and would not affect other cars traveling to other destinations much at all.

The result is that more tracer will arrive in cortical region 530 with deep lesion 510 relative to cortical lesion 560. In addition, with deep lesion 510, the peak tracer concentration will be delayed more with respect to the normal tracer curve as compared to the delay caused by cortical lesion 560. This greater delay occurs because the tracer must travel a greater distance, via collateral arterioles, from the lesion to cortical region 530 in brain 500.

In summary, as compared to a normal tracer curve, a cortical lesion will cause the tracer peak to be delayed by a small amount and have a significantly reduced peak concentration, while a sub-cortical or deep lesion will cause a longer delay in the peak arrival of the tracer and a smaller reduction in the peak concentration. Thus, thresholds on both the temporal and concentration characteristics will enable discernment of deep and cortical lesions. This threshold approach is also supported by the spatial extent (size) of the abnormal blood flow in the cortex. A small spatial extent will be consistent with a cortical lesion, while a large spatial extent will suggest a deep lesion. Thresholds can be set as follows: if (1) the peak delay relative to the normal curve is greater than about 2 seconds, (2) the peak amplitude is reduced by less than about 50% of the normal peak amplitude, (3) the spatial extent of the blood flow anomaly is greater than about 20 mm in diameter, and/or (4) the minimal period of time required for passage of a dye bolus at a detection point is about 2 or more seconds longer than a normal reference period of time, then a deep ischemic event is indicated.

Of course, the detection of any ischemic event, whether deep or cortical, is based on thresholds broader than the ones described immediately above. An ischemic event is detected if (1) the peak delay relative to the normal curve is greater than about 1 second, (2) the peak amplitude is reduced as compared to the normal peak amplitude, (3) a blood flow anomaly is detected, and/or (4) the minimal period of time required for passage of a dye bolus at a detection point is longer than a normal reference period of time.

If the size of the region of abnormal blood flow is measured and mapped to a particular region of the brain, this information can be used to determined which blood vessel and where along its path the blockage has occurred. This is possible because the architecture of brain vasculature is well known and has been exhaustively catalogued in the human population. See, e.g., Kretschmann et al., "Arteries of the Brain and their Vascular Territories," In: *Cranial Neuroimaging and Clinical Neuroanatomy*, Thieme Medical Publishers, Inc., New York, pp 191–199, 1992. In other words, given the known blood vessel path, direction of blood flow, and interconnections among arteries and arterioles, one can deduce the location of the blockage responsible for the cortical blood flow abnormality detected by DOT. For example, referring back to FIGS. 6A and 6B, the locations of lesions 510 and 560 can be deduced from the position and size of affected regions 520 and 570, respectively.

The invention will be further described in the following examples, which do not limit the scope of the invention defined in the claims.

EXAMPLES

Example 1

Distinguishing Deep Ischemic Events from Cortical Ischemic Events

One can distinguish a deep ischemic event from a cortical ischemic event by the differences in the hemodynamic spatio-temporal signatures generated by DOT. For a patient suffering from a stroke, a health care provider first withdraws a 1 ml volume of blood from the patient and mixes the blood with 1 ml of a solution containing 0.1 mg/kg body weight of indocyanine green dye (Pulsion-green, Pulsion, Munich, Germany) dissolved in water. After a period of about 15 seconds to allow binding of the dye to plasma proteins, the 2 ml mixture is injected as a bolus into the patient through a venous catheter in the arm.

The patient's head is first fitted with a helmet containing optodes emitting red light at 780 nm and optode detectors spaced throughout the scalp surface covered by the helmet. Light is emitted by the a laser and passes through the optodes and into the brain through the scalp and skull of the patient. Any light that is reflected and/or scattered by the brain and passes out through the scalp and skull is detected. The amplitude of detected light at a point above the scalp is inversely correlated with the concentration of dye in the cortical region of the brain below that point.

Figures 7A, 7B:
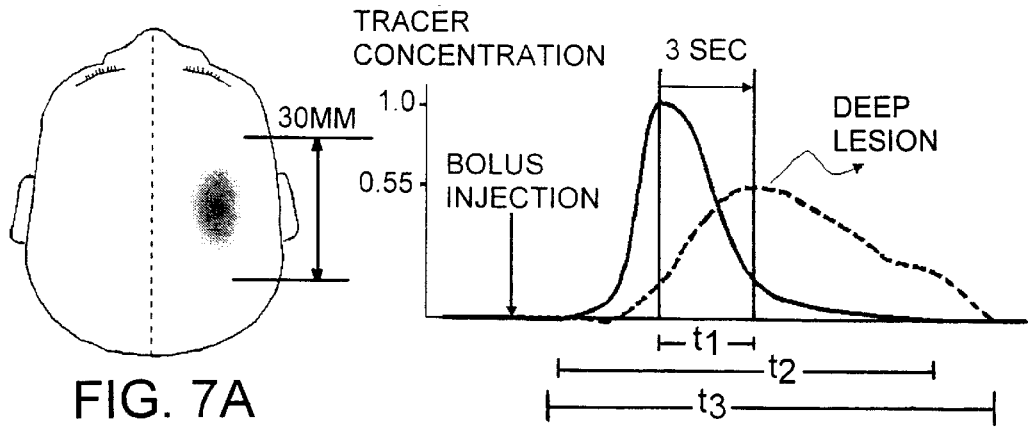
FIG. 7A is a schematic drawing of a human head, showing the spatial distribution of blood flow abnormalities arising from a deep ischemic event.
FIG. 7B is a graph of time versus tracer concentration for the abnormality seen in FIG. 7A.

If the patient is experiencing an ischemic event in a deep portion of the brain, a diffuse blood flow abnormality will be evident in a cortical region of the brain. As shown in FIGS. 7A and 7B, as the dye bolus passes the cortical region of the brain adjacent to a deep ischemic event, the bolus is both diffuse and delayed in comparison to a reference dye bolus trace. The reference dye bolus trace can be an averaged or estimated normal trace, an actual trace of the patient's brain under normal (i.e., without an ischemic event) conditions, or a trace of a normal matched portion of the brain (e.g., an unaffected hemisphere of the brain). As indicated in the graph of FIG. 7B, the peak concentration of dye in the affected cortical region is about 55% of the peak normal peak concentration, showing the reduction in the amount of dye moving through the cortical region that would be expected by a deep ischemic event.

The deep ischemic event also leads to an increase of about 3 seconds in the time it takes the peak concentration to be detected after the bolus is injected or passes a reference 965 point as compared to a normal peak concentration ($t_1$), showing that the bolus of dye moving through the cortical region of the brain has been delayed by a deep ischemic event. Finally, the size of the blood flow abnormality (30 mm at the longest diameter) is indicated by the longer period of time required for the bolus to completely traverse the affected cortical region ($t_3$), as compared to the time required for the bolus to traverse the unaffected region ($t_2$). In this instance, $t_3$ is about 3 seconds longer than $t_2$. In other words, the minimal amount of time required for the dye concentration to advance from zero to the peak, then back down to zero is far longer than under normal conditions. This result is indicative of a disruption of the flow of the dye bolus by the deep ischemic event, of which only the collateral effects of the disruption in the cortex is being detected by DOT. See general discussion above under "Distinguishing a Cortical Ischemic Event from a Deep Ischemic Event in the Brain."

Figures 8A, 8B:
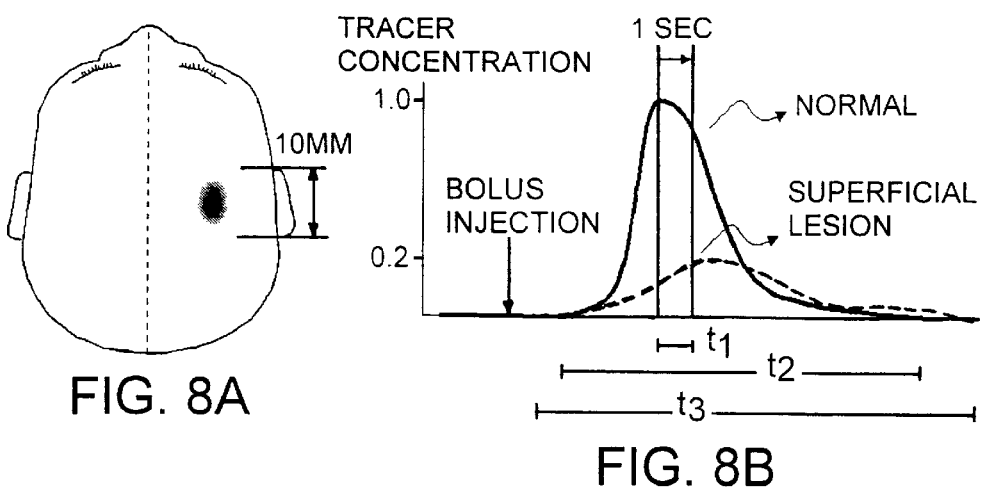
FIG. 8A is a schematic drawing of a human head, showing the spatial distribution of blood flow abnormalities arising from a cortical ischemic event.
FIG. 8B is a graph of time versus tracer concentration for the abnormality seen in FIG. 8A.

In contrast, if the patient is experiencing an ischemic event in the cortex of the brain, several distinguishing characteristics of the abnormal trace of dye concentration can be seen in FIGS. 8A and 8B. First, as shown in FIG. 8B, the peak dye concentration is reduced by a greater amount (80%) from normal than is seen for a deep ischemic event (e.g., 45% in FIG. 7B) because the source of the dye flow blockage, rather than its downstream effects, is directly detected by DOT. Second, the increase in the time required for the peak concentration to travel from a reference point, e.g., bolus injection, to the detection site, relative to normal ($t_1$) is only about 1 second because the detected region is closer to the source of the ischemic event. Third, the minimal amount of time needed for the dye concentration to vary from zero to a peak, and back down to zero ($t_3$) is only about 1 second longer than that for the normal trace ($t_2$). These characteristics are analogous to the "ripple effect" seen on the water's surface formed from a pebble thrown into a pond. As observations are made closer to the ischemic event, the effect is both briefer and more intense than when the observation is made farther away from the event.

Example 2

Detecting a Brain Bleed in a Human Stroke Patient

A brain bleed can also be detected by DOT following the procedure described in Example 1, except that a measurement is made at a single time point after the dye is distributed uniformly throughout the circulatory system and the brain, instead of measuring the movement of a dye bolus through the brain over time. FIGS. 9A and 9B show the head of an individual experiencing a brain bleed and the expected position-dependent trace of the dye concentration, respectively. The dye is shown by the hatched region, and the pooling of blood at the bleed is shown by the clear region within the hatched region, with the source of the bleed indicated as a dot. As traced in the graph of FIG. 9B, the dye concentration along line A passing through the source of the bleed differs from a normal trace by the presence of a region of a lower concentration of dye. This phenomenon is caused by the clotting and blood vessel constriction associated with the bleed, which inhibits the dye from infiltrating the bleed region. However, the clotting and blood vessel constriction would not be apparent immediately after the bleed begins, since some time is required for these physiological and biochemical events to occur. Regions in the brain adjacent to the bleed area are not affected.

Alternatively, a brain bleed can be detected by allowing sufficient time for the dye to infiltrate the bleed. Once the dye enters the bleed, the dye is trapped in the bleed by the clotting and blood vessel constriction mentioned above. Meanwhile, the dye in the rest of the circulation is being removed from the body, e.g., by the liver, or degrades. If a measurement of dye concentration is made at this later time point, the presence of a bleed can be seen by an inverse of the phenomenon shown in FIGS. 9A and 9B; namely, that a higher dye concentration is seen in the bleed region, while the rest of the brain exhibits a lower or zero dye concentration. While at this later time (about 10 minutes following bolus injection) the dye concentration in the bleed may be greater than the surrounding tissue, it will always be smaller than the peak concentration observed in the surrounding tissue at earlier times (about 1 minute following injection).

Example 3

Modeling Blood Flow

Tubes were impregnated in a solution containing Intralipid™ (Flock et al., Lasers in Surgery and Medicine 12:510–519, 1992; and Van Staveren et al., Applied Optics 30:4507–4514, 1991) and india ink. Intralipid™, an aqueous suspension of lipid droplets, is a common, fat-rich supplement given intravenously to patients in a hospital. The concentration of Intralipid™ in the solution was adjusted to give the solution light scattering properties similar to that in a human brain, the concentration of india ink was adjusted to give the solution light absorption properties similar to that in a human brain. A dilute india ink solution having absorption properties similar to blood was passed through the tubes. The liquid was circulated through the tubes with a pulsatile pump to give a temporal flow distribution similar to that found in arteries. Optodes were then placed on the surface of the slab to deliver light (780 nm) and collect the diffusely remitted light. The separation between optodes was adjusted to 1, 2, 3, and 4 cm for different experiments. A bolus of concentrated india ink (dye) was then injected into the tubes upstream of the position of the optodes. As the dye flowed past the optodes, the light detected decreased in intensity due to the increased absorption of light by the dye. After the dye agent passed the imaging area, the optical signal returned to baseline. The experiment was then repeated at a different flow speed.

The amplitude of detected light at the two flow speeds and with a optode separation of 4 cm is graphed in FIG. 10. The "Fast Flow" (shown as the first inverted peak at about 5 seconds) is about 4 times as fast as the "Slow" speed (shown as the second inverted peak at about 17 seconds). "Fast Flow" data points are graphed as solid square symbols, while the "Slow" flow symbols are graphed as solid circles. The graph shows that distinct variations in amplitude could be detected as the bolus passed through the region imaged, indicating that cerebral blood flow could be monitored using DOT.

Example 4

Detection of a Brain Bleed in a Piglet Model Using a Calibration Method

A piglet model was used in this study. The experimental set-up was a hybrid system of diffuse optical tomography and X-ray CT. Measurements were made on the bench of the X-ray scanner.

A one-week old piglet weighing 3 kg was sedated, intubated, and ventilated during the experiment. The femoral artery was catheterized for continuous blood pressure monitoring, fluid infusions, and blood extractions. Some of the blood taken from the femoral artery was delivered through two small needles inserted 2 cm through scalp, skull, and brain tissue to produce an artificial brain bleed. The separation of insertion points for the two needles was about 2 cm. The combined thickness of the scalp and skull was about 1 cm, so the blood was injected into the brain at a depth of about 1 cm. The injection speed was controlled by a step motor at a rate of 42 $\mu$l/min. A total of 625 $\mu$l of blood was injected in 15 minutes for each bleed. Images were reconstructed every 15 seconds. Bleed A was created first, then bleed B. The optical probe was placed on top of the piglet's head.

Figure 11:
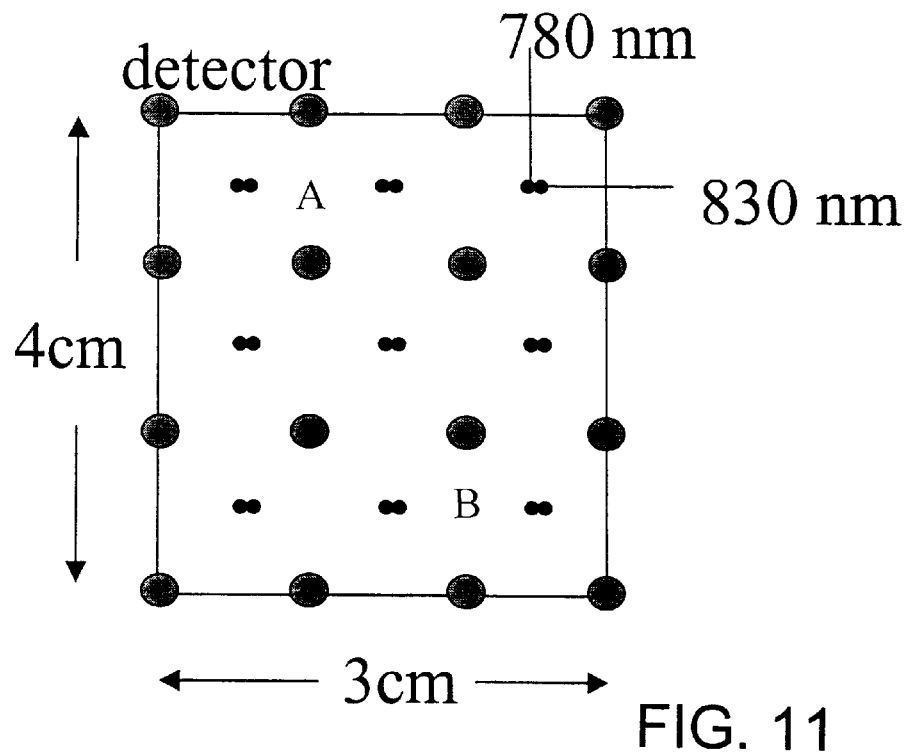
FIG. 11 is a schematic diagram of the optical arrangement of the sources and detectors used in Example 5 below.

Referring to FIG. 11, the probe has 16 detectors (large circles) and 9 sources (pairs of small circles) at each of 780 nm and 830 nm. The positions of bleeds A and B relative to the probe are also shown in FIG. 11. Before injecting bleed A, a baseline was measured and used to find the coupling coefficient of each source-detector channel and also the background optical properties. The calculated absorption and effective scattering coefficients were 0.0672 cm$^{-1}$ and 8.44 cm$^{-1}$, respectively, at 780 nm, and 0.0666 cm$^{-1}$ and 7.61 cm$^{-1}$, respectively, at 830 nm. These values correspond to an oxygen saturation (SO$_2$) of 58% and a total hemoglobin content (HbT) of 78 $\mu$l/mol. After bleed A was generated, another baseline was measured before injecting bleed B. X-ray CT images were taken after the optical measurements to identify the positions of the bleeds.

2D images were reconstructed based on the DOT measurements using simultaneous iterative reconstruction technique (SIRT) and assuming that the piglet head is semi-infinite. FIGS. 12A–12D show the time-course of the reconstructed images of bleed A at both wavelengths, with and without using the calibration method described in detail above to correct the DOT measurements. FIGS. 12A–12D show that the application of the calibration method greatly reduces the presence of artifacts in the bottom and right sides of the images. The calibration method also improves the image amplitude.

Figure 13A:
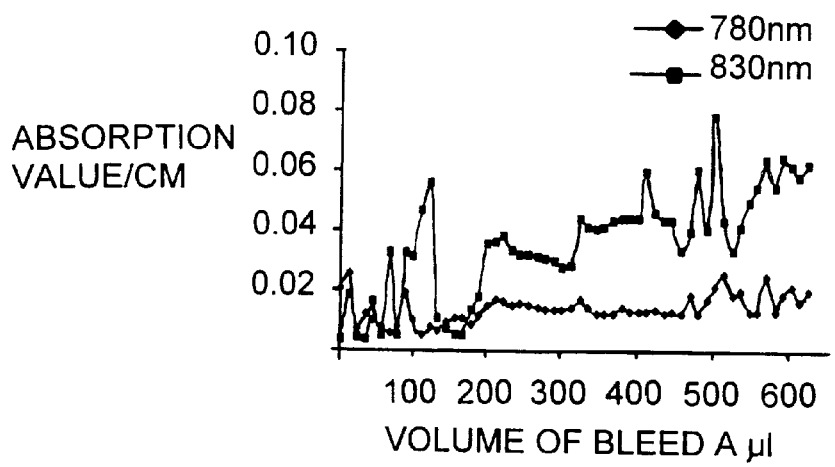
FIGS. 13A and 13B are graphs of peak image values derived from the images of FIGS. 12A–12D.
Figure 13B:
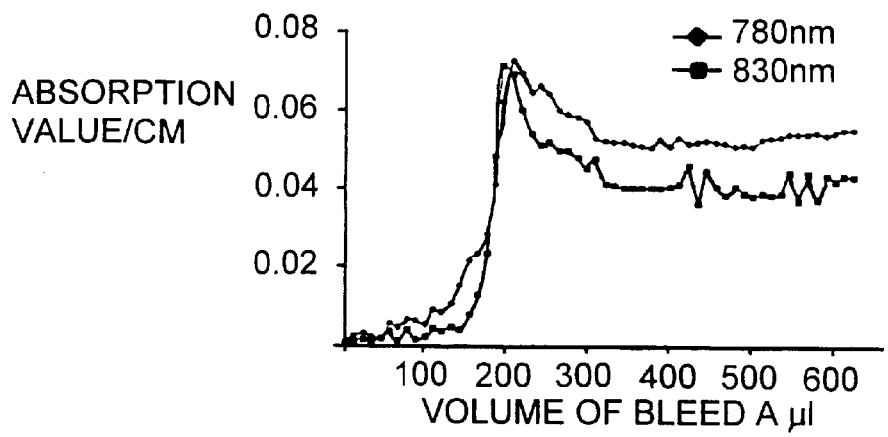

FIGS. 13A and 13B show a time-course plot of the peak image value of bleed A at the two wavelengths. Without calibration (FIG. 13A), the plot is noisy with no clear build up of the bleed. After the calibration (FIG. 13B), however, the development of the bleed is clearly visible.

Figure 14:
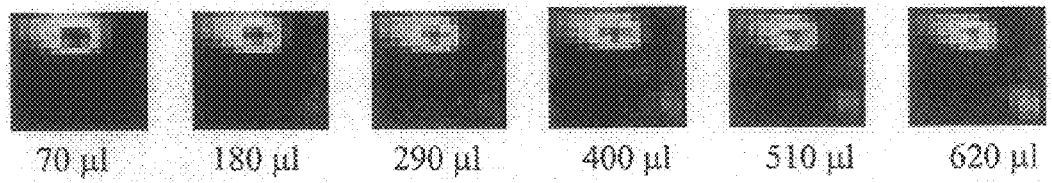
FIG. 14 is an additional reconstructed image of the experimental data from Example 5 below.

FIG. 14 shows time-course images of both bleeds A and B as the volume of bleed B was increased. The base line and coupling coefficient were the same as those used in reconstructing images of bleed A. The respective intensities of the A and B bleeds differ because their depths differ.

These results indicate that the use of a dye bolus in conjunction with the calibration method described herein further facilitate the methods of detecting deep ischemic events or bleeds in the brain.

Example 5

Monitoring Cerebral Blood Flow in an Adult Human

A 100 mW, 808 nm laser diode coupled to a 1 mm diameter fused silica fiber was used to deliver light to an adult human head. Four diode detectors were coupled to the scalp via 3 mm diameter plastic fibers. The collecting fibers were positioned 1, 2, 3, and 4 cm from the emitting fiber. These four separations were chosen to discriminate between scalp signals and skull signals. Measurements made at 1 and 2 cm separations were sensitive to changes in the optical properties of only the skull and scalp. On the other hand, measurements made at 3 and 4 cm separations were sensitive to changes in the optical properties of the brain, skull, and scalp. The remitted intensity at the four positions was sampled at 4 Hz. Baseline data was collected for 10 seconds, followed by the bolus injection. The bolus consisted of a 2 ml saline solution of 40 mg of indocyanine green injected into a vein in the arm of the volunteer. This injection was immediately followed by a 10 ml saline flush.

Figure 15:
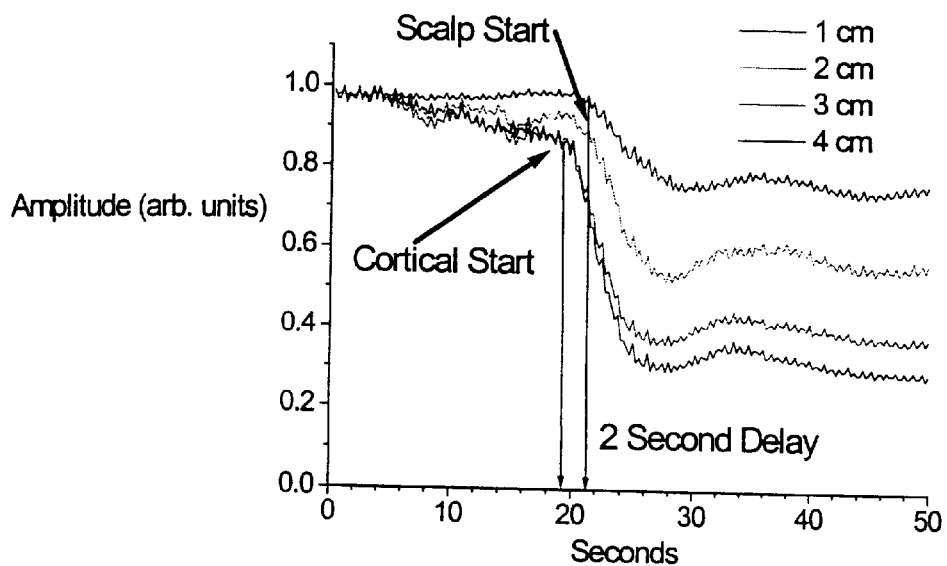
FIG. 15 is a graph of time versus amplitude obtained in the experiment of Example 6.
Figure 12A:
FIGS. 12A–12D are reconstructed DOT images of experimental data from Example 5 below.
Figure 12B:
Figure 12C:
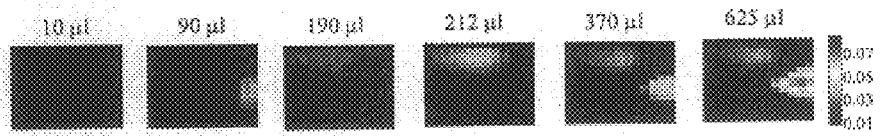
Figure 12D:
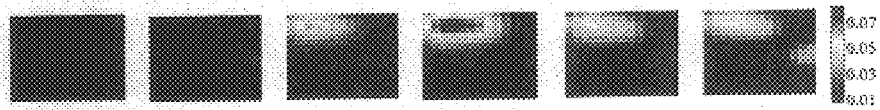

The data is summarized in the graph of FIG. 15, showing the attenuation of the optical signal caused by passing of the bolus of indocyanine green through the brain of the adult human volunteer. The results indicate that, at 20 seconds following the injection of the dye bolus, the signal at 3 and 4 cm separations dropped significantly, while the drop in the signals at 1 and 2 cm separations was delayed by about 2 seconds. The delay at 1 and 2 cm separations indicated that the signal decay at the 3 and 4 cm separation for the initial 2 seconds was entirely due to the arrival of indocyanine green in the brain. The small increases in each signal at about 34 seconds resulted from the re-circulation of the indocyanine green bolus.

It appeared that the concentration of indocyanine green actually drops by more than a factor of ten during re-circulation. At first thought, this result should have led to a much greater increase in the optical signal, and, in fact, the signal might have been expected to return to baseline. However, the dye concentration is likely large enough to have saturated the optical attenuation. This is further evidenced by uniform distribution of the signal during the second passage of the bolus, which has a concentration about 10 times smaller than the bolus of the first passage.

These results show that detecting a dye bolus in an adult brain is possible. The blood flow can then be calculated by applying Fick's principle as described in Patel et al., supra; Edwards et al., Lancet 2:770–771, 1988; Edwards et al., J. App. Physiol. 75:1884–1889, 1993; or Kuebler et al., J. Cerebral Blood Flow Met. 18:445–456, 1988.

OTHER EMBODIMENT

It is to be understood that while the invention has been described in conjunction with the detailed description thereof, the foregoing description is intended to illustrate and not limit the scope of the invention, which is defined by the scope of the claims. Other aspects, advantages, and modifications are within the scope of the following claims.

For example, the methods of the invention can be accomplished with any combination of one or more fluorescent and/or non-fluorescent dyes injected (e.g., as a bolus) into the blood stream of an individual.

What is claimed is:

1. A method of detecting an ischemic event in a brain in a subject, the method comprising administering a dye bolus into the bloodstream of the subject;

directing light into the brain of the subject;

detecting light emitted from the brain over time at a detection location, wherein the dye is present in the brain for at least a portion of the detection time, and the light emitted from the brain in the presence of the dye is different from the light emitted from the brain in the absence of the dye, the magnitude of the difference corresponding to the concentration of the dye;

establishing a reference time period corresponding to the time a peak concentration of a dye bolus takes to reach the detection location in a normal brain;

determining a subject time period corresponding to the time a peak concentration of the dye bolus takes to reach the detection location in the subject; and comparing the subject time period with the reference time period, wherein a subject time period 1 or more seconds longer than the reference time period indicates an ischemic event in the brain.

2. The method of claim 1, wherein the dye is indocyanine green.

3. The method of claim 1, wherein the difference is in the amplitude of light.

4. The method of claim 1, wherein the subject is a mammal.

5. The method of claim 4, wherein the mammal is a human.

6. The method of claim 1, comprising directing light into the brain through the scalp from a plurality of light sources and detecting light emitted from the brain using a plurality of photodetectors.

7. The method of claim 1, wherein the light is emitted and detected using a system comprising:

at least two optical sources which during operation emit light into a sample at spatially separated locations;

at least two optical detectors positioned to receive light emitted from the sample at spatially separated locations in response to the light emitted from the sources, wherein the signal $g(i,j)$ produced by the $j^{th}$ detector in response to the optical radiation from the $i^{th}$ source can be expressed as $g(i,j)=S^i D^j f(i,j)$, where $f(i,j)$ depends only on the properties of the head of the subject, $S^i$ is a coupling coefficient for the $i^{th}$ source, and $D^j$ is a coupling coefficient for the $j^{th}$ detector; and an analyzer which during operation calculates the value of the product $S^i D^k$ for at least one of the source-detector pairs based on the signals produced by the detectors and simulated values of $f(i,j)$ corresponding to a model of the optical properties of the sample.

8. The method of claim 1, wherein light is directed by at least two optical sources, light is detected by at least two optical detectors, the sources couple light into the brain at spatially separated locations, and the detectors are positioned to receive light emitted from the sample at spatially separated locations and generate signals in response to the light from the sources; the method further comprising providing the signals generated by the detectors, wherein the signal $g(i,j)$ generated by the $j^{th}$ detector in response to the optical radiation from the $i^{th}$ source can be expressed as $g(i,j)=S^i D^j f(i,j)$, where $f(i,j)$ depends only on the properties of the sample, $S^i$ is a coupling coefficient for the $i^{th}$ source, and $D^j$ is a coupling coefficient the $j^{th}$ detector; and calculating the value of the product $S^i D^k$ for at least one of the source-detector pairs based on the signals generated by the detectors and simulated values of $f(i,j)$ corresponding to a model of the optical properties of the brain.

9. A method of detecting an ischemic event in a brain in a subject, the method comprising administering a dye bolus into the bloodstream of the subject;

directing light into the brain of the subject;

detecting light emitted from the brain over time at a detection location, wherein the dye is present in the brain for at least a portion of the detection time, and the light emitted from the brain in the presence of dye is different from the light emitted from the brain in the absence of the dye, the magnitude of the difference corresponding to the concentration of the dye;

establishing a peak reference concentration of a dye bolus administered to a subject with a normal brain at the detection location;

determining a peak subject concentration of the dye bolus at the detection location; and comparing the peak subject concentration with the peak reference concentration, wherein a peak subject concentration below the peak reference concentration indicates an ischemic event in the brain.

10. The method of claim 9, wherein the dye is indocyanine green.

11. The method of claim 9, wherein the difference is in the amplitude of light.

12. The method of claim 9, wherein the subject is a mammal.

13. The method of claim 12, wherein the mammal is a human.

14. The method of claim 9, comprising directing light into the brain through the scalp from a plurality of light sources and detecting light emitted from the brain using a plurality of photodetectors.

15. A method of detecting an ischemic event in a brain in a subject, the method comprising administering a dye bolus into the bloodstream of the subject;

directing light into the brain of the subject;

detecting light emitted from the brain over time at a detection location, wherein the dye is present in the brain for at least a portion of the detection time, and the light emitted from the brain in the presence of dye is different from the light emitted from the brain in the absence of the dye, the magnitude of the difference corresponding to the concentration of the dye;

establishing a reference time period corresponding to the time for the concentration of a dye bolus to vary from a threshold concentration to a peak concentration and back to the threshold concentration at the detection location in a normal brain;

determining a subject time period corresponding to the time for the concentration of the dye to vary from the threshold concentration to a peak concentration and back to the threshold concentration at the detection location; and comparing the subject time period with the reference time period, wherein a subject time period longer than the reference time period indicates an ischemic event in the brain.

16. The method of claim 15, wherein the dye is indocyanine green.

17. The method of claim 15, wherein the difference is in the amplitude of light.

18. The method of claim 15, wherein the subject is a mammal.

19. The method of claim 18, wherein the mammal is a human.

20. The method of claim 15, comprising directing light into the brain through the scalp from a plurality of light sources and detecting light emitted from the brain using a plurality of photodetectors.

21. The method of claim 15, wherein the threshold concentration is 10% on a volume basis.

22. A method of detecting an ischemic event in a brain in a subject, the method comprising administering a dye bolus into the bloodstream of the subject;

directing light into the brain of the subject;

detecting light emitted from the brain over time at a detection location, wherein the dye is present in the brain for at least a portion of the detection time, and the light emitted from the brain in the presence of the dye is different from the light emitted from the brain in the absence of the dye, the magnitude of the difference corresponding to the concentration of the dye;

establishing a reference map of cortical blood flow in a normal brain;

obtaining a subject map of cortical blood flow in the subject; and comparing the reference map with the subject map, wherein a continuous region of decreased blood flow in the subject map, compared to the reference map indicates an ischemic event in the brain.

23. The method of claim 22, wherein the dye is indocyanine green.

24. The method of claim 22, wherein the difference is in the amplitude of light.

25. The method of claim 22, wherein subject is a mammal.

26. The method of claim 25, wherein the mammal is a human.

27. The method of claim 22, comprising directing light into the brain through the scalp from a plurality of light sources and detecting light emitted from the brain using a plurality of photodetectors.

28. A method of detecting an ischemic event in a brain in a subject, the method comprising administering a dye bolus into the bloodstream of the subject;

directing light into the brain of the subject;

detecting light emitted from the brain over time at a detection location, wherein the dye is present in the brain for at least a portion of the detection time, and the light emitted from the brain in the presence of the dye is different from the light emitted from the brain in the absence of the dye, the magnitude of the difference corresponding to the concentration of the dye;

establishing (1) a first reference time period corresponding to the time a peak concentration of a dye bolus takes to reach the detection location in a normal brain, (2) a peak reference concentration for a dye bolus administered to a subject with a normal brain at the detection location, and (3) a second reference time period corresponding to the time for the concentration of a dye bolus to vary from a threshold concentration to a peak concentration and back to threshold concentration at the detection location in a normal brain;

determining (1) a first subject time period corresponding to the time a peak concentration of the dye bolus takes to reach the detection location in the subject, (2) a peak subject concentration of the dye bolus at the detection location, and (3) a second subject time period corresponding to the time for the concentration of the dye to vary from the threshold concentration to a peak concentration and back to the threshold concentration at the detection location; and comparing the first subject time period with the first reference time period, the peak subject concentration with the peak reference concentration, and the second subject time period with the second reference time period;

wherein a first subject time period 1 or more seconds longer than the reference time period, a peak subject concentration below the peak reference concentration, and a second subject time period longer than the second reference time period together indicate an ischemic event in the brain.

29. A method of detecting an ischemic event in a brain in a subject, the method comprising comparing (1) a subject time period corresponding to the time a peak concentration of a dye bolus takes to reach a detection location on the brain of a subject with (2) a reference time period corresponding to the time a peak concentration of a dye bolus takes to reach the detection location in a normal brain, wherein a subject time period 1 or more seconds longer than the reference time period indicates an ischemic event in the brain.

30. A method of detecting an ischemic event in a brain in a subject, the method comprising comparing (1) a peak subject concentration of a dye bolus at a detection location on the brain of the subject with (2) a peak reference concentration of a dye bolus administered to a subject with a normal brain at the detection location, wherein a peak subject concentration below the peak reference concentration indicates an ischemic event in the deep portion of the brain.

31. A method of detecting an ischemic event in a brain in a subject, the method comprising comparing (1) a subject time period required for the concentration of the dye to vary from a threshold concentration to a peak concentration and back to threshold concentration at a detection location on the brain of a subject with (2) a reference time period corresponding to the time for the concentration of a dye to vary from the threshold concentration to a peak concentration and back to threshold concentration at the detection location on a normal brain, wherein a subject time period longer than the reference time period indicates an ischemic event in the brain.

32. A method of detecting an ischemic event in a brain in a subject, the method comprising comparing (1) a subject map of cortical blood flow in the brain of a subject with (2) a reference map of cortical blood flow in a normal brain, wherein a continuous region of decreased blood flow in the subject map, compared to the reference map, of at least 20 mm at the longest diameter indicates an ischemic event in the brain.

33. A method of detecting a brain bleed in a subject, the method comprising administering a dye into the bloodstream of the subject;

directing light from a light source into the brain of the subject;

detecting light emitted from the brain while the dye is present in a portion of the brain, the light emitted from the brain in the presence of the dye being different from the light emitted from the brain in the absence of the dye, the magnitude of the difference corresponding to the concentration of the dye, wherein the detecting step is performed while the dye is detectable in the blood circulation of the subject; and determining the concentration of the dye in the portion of the brain, wherein a region of the portion with a lower concentration of the dye than an adjacent region of the portion indicates a brain bleed.

34. The method of claim 33, wherein no detectable dye is present in the region of the portion.

35. The method of claim 33, wherein the dye is indocyanine green.

36. The method of claim 33, wherein the subject is a mammal.

37. The method of claim 36, wherein the mammal is a human.

38. The method of claim 33, wherein the difference is in the amplitude of light.

39. A method of detecting a brain bleed in a subject, the method comprising administering a dye into the bloodstream of the subject;

directing light from a light source into the brain of the subject;

detecting light emitted from the brain while the dye is present in a portion of the brain, the light emitted from the brain in the presence of the dye being different from the light emitted from the brain in the absence of the dye, the magnitude of the difference corresponding to the concentration of the dye, wherein the detecting step is performed after the initial dye concentration in the blood circulation of the subject has been reduced; and determining the concentration of the dye in the portion of the brain, wherein a region of the portion with a higher concentration of the dye than an adjacent region of the portion indicates a brain bleed.

40. The method of claim 39, wherein no detectable dye is present in the blood circulation of the subject.

41. The method of claim 39, wherein the dye is indocyanine green.

42. The method of claim 39, wherein the subject is a mammal.

43. The method of claim 42, wherein the mammal is a human.

44. The method of claim 39, wherein the difference is in the amplitude of light.

45. A method of detecting an ischemic event in a deep portion of a brain, the method comprising detecting an ischemic event in the brain of a subject using the method of claim 1, wherein a subject time period of 2 or more seconds longer than the reference time period indicates an ischemic event in a deep portion of the brain.

46. A method of detecting an ischemic event in a deep portion of a brain, the method comprising detecting an ischemic event in the brain of a subject using the method of claim 9, wherein a peak subject concentration between 100% and 50% of the peak reference concentration indicates an ischemic event in a deep portion of the brain.

47. A method of detecting an ischemic event in a deep portion of a brain, the method comprising detecting an ischemic event in the brain of a subject using the method of claim 9, wherein a peak subject concentration below the peak reference concentration but at least 50% of the peak reference concentration indicates an ischemic event in a deep portion of the brain.

48. A method of detecting an ischemic event in a deep portion of a brain, the method comprising detecting an ischemic event in the brain of a subject using the method of claim 22, wherein a continuous region of decreased blood flow in the subject map, compared to the reference map, of at least 20 mm at the longest diameter, indicates an ischemic event in the deep portion of the brain.

49. The method of claim 22, further comprising comparing the position of the region of decreased blood flow with a map of known brain vasculature; and extrapolating the position of the ischemic event in the brain of the subject.

* * * * *